(12) United States Patent
Kohara et al.

(10) Patent No.: US 8,957,199 B2
(45) Date of Patent: Feb. 17, 2015

(54) OLIGORIBONUCLEOTIDE OR PEPTIDE NUCLEIC ACID CAPABLE OF INHIBITING ACTIVITY OF HEPATITIS C VIRUS

(75) Inventors: Michinori Kohara, Tokyo (JP); Masayuki Sudo, Kanagawa (JP)

(73) Assignees: Chugai Seiyaku Kabushiki Kaisha, Tokyo (JP); Tokyo Metropolitan Institute of Medical Science, Tokyo (JP)

( * ) Notice: Subject to any disclaimer, the term of this patent is extended or adjusted under 35 U.S.C. 154(b) by 0 days.

(21) Appl. No.: 13/130,673

(22) PCT Filed: Nov. 26, 2009

(86) PCT No.: PCT/JP2009/069934
§ 371 (c)(1),
(2), (4) Date: Jul. 27, 2011

(87) PCT Pub. No.: WO2010/061881
PCT Pub. Date: Jun. 3, 2010

(65) Prior Publication Data
US 2011/0281271 A1    Nov. 17, 2011

(30) Foreign Application Priority Data
Nov. 26, 2008 (JP) ................................. 2008-301764

(51) Int. Cl.
*C07H 21/04* (2006.01)
*C12N 15/11* (2006.01)
*C12N 15/113* (2010.01)

(52) U.S. Cl.
CPC ..................................... *C12N 15/113* (2013.01)
USPC ....................................... 536/24.5; 514/44 A

(58) Field of Classification Search
None
See application file for complete search history.

(56) References Cited

U.S. PATENT DOCUMENTS

| 3,000,910 | A | 9/1961 | Birkenmeyer et al. |
| 3,210,386 | A | 10/1965 | Birkenmeyer et al. |
| 3,389,051 | A | 6/1968 | Fred et al. |
| 3,928,572 | A | 12/1975 | Kluepfel et al. |
| 5,336,507 | A | 8/1994 | Na et al. |
| 5,518,879 | A | 5/1996 | Merrill et al. |
| 5,863,716 | A | 1/1999 | Haldar et al. |
| 5,976,781 | A | 11/1999 | Haldar et al. |
| 6,303,350 | B1 | 10/2001 | Takesako et al. |
| 7,217,793 | B2 | 5/2007 | Kobayashi et al. |
| 7,378,446 | B2 | 5/2008 | Sudoh et al. |
| 7,776,918 | B2 | 8/2010 | Aoki et al. |
| 8,183,005 | B1 | 5/2012 | Sudo et al. |
| 2002/0127203 | A1 | 9/2002 | Albrecht |
| 2006/0128617 | A1 | 6/2006 | Kohara et al. |
| 2006/0194870 | A1 | 8/2006 | Sudoh et al. |
| 2006/0217434 | A1 | 9/2006 | Aoki et al. |
| 2006/0264389 | A1 | 11/2006 | Bhat et al. |
| 2007/0087984 | A1 | 4/2007 | Hu et al. |
| 2007/0141133 | A1 | 6/2007 | Wang et al. |
| 2008/0027088 | A1 | 1/2008 | Homan et al. |
| 2008/0193512 | A1 | 8/2008 | Niitsu et al. |
| 2009/0022687 | A1 | 1/2009 | Matsumoto et al. |
| 2009/0175930 | A1 | 7/2009 | Yagi et al. |
| 2011/0160252 | A1 | 6/2011 | Mizokami et al. |

FOREIGN PATENT DOCUMENTS

| CA | 2 652 333 | 11/2007 |
| EP | 1 591 524 | 11/2005 |
| EP | 1 593 378 | 11/2005 |
| EP | 1 795 206 | 6/2007 |
| JP | 6-211646 | 8/1994 |
| JP | 7-173123 | 7/1995 |
| JP | 2002-520038 | 7/2002 |
| JP | 2002-538099 | 11/2002 |
| JP | 2003-528131 | 9/2003 |
| JP | 2004-511513 | 4/2004 |
| JP | 2005-533108 | 11/2005 |
| JP | 2005-533824 | 11/2005 |
| JP | 2006-077004 | 3/2006 |
| JP | 2007-513122 | 5/2007 |
| JP | 3921227 | 5/2007 |
| JP | 2007-515452 | 6/2007 |
| JP | 2007-169252 | 7/2007 |
| JP | 2008-501729 | 1/2008 |
| JP | 2008-501730 | 1/2008 |
| JP | 2008-050375 | 3/2008 |
| JP | 2008-054681 | 3/2008 |
| JP | 2008-530215 | 8/2008 |
| WO | WO 94/18157 | 8/1994 |

(Continued)

OTHER PUBLICATIONS

Watanabe et al, Intracellular-diced dsRNA has enhanced efficacy for silencing HCV RNA and overcomes variation in the viral genotype, Feb. 23, 2006, Gene Therapy, 13:883-892.*
Ketting et al, Dicer functions in RNA interference and in synthesis of small RNA involved in developmental timing in *C. elegans*, 2001, Genes Dev., 15:2654-2659.*
Supplementary European Search Report for App. Ser. No. EP 07 74 3451, mailed Oct. 17, 2011, 10 pages.
USPTO Interview Summary in U.S. Appl. No. 11/659,779, dated Oct. 26, 2011, 2 pages.
Fish & Richardson P.C., Amendment in Reply to Action dated May 13, 2011 in U.S. Appl. No. 11/659,779, filed Nov. 10, 2011, 17 pages.
USPTO Interview Summary in U.S. Appl. No. 11/659,779, dated Dec. 8, 2011, 2 pages.

(Continued)

*Primary Examiner* — Tracy Vivlemore
*Assistant Examiner* — Kate Poliakova-Georgantas
(74) *Attorney, Agent, or Firm* — Fish & Richardson P.C.

(57) ABSTRACT

The present inventors focused on siE sequences that have been thought to show RNAi activity against HCV viral RNAs, and mainly selected the D5-50 and D5-197 regions present within the IRES region, and carried on the analysis. As a result, the present inventors successfully identified siRNA sequences that exhibit a more effective RNAi activity against hepatitis C virus RNAs. Furthermore, the siRNAs were demonstrated to have a significant inhibitory effect on HCV propagation in an in vivo system.

15 Claims, 8 Drawing Sheets

(56) References Cited

FOREIGN PATENT DOCUMENTS

| WO | WO 98/20109 | 5/1998 |
|---|---|---|
| WO | WO 98/56755 | 12/1998 |
| WO | WO 00/03683 | 1/2000 |
| WO | WO 00/37097 | 6/2000 |
| WO | WO 00/51572 | 9/2000 |
| WO | WO 01/72283 | 10/2001 |
| WO | WO 02/32414 | 4/2002 |
| WO | WO 02/48325 | 6/2002 |
| WO | WO 2004/002422 | 1/2004 |
| WO | WO 2004/007512 | 1/2004 |
| WO | WO 2004/071503 | 8/2004 |
| WO | WO 2004/078127 | 9/2004 |
| WO | WO 2004/078974 | 9/2004 |
| WO | WO 2005/005372 | 1/2005 |
| WO | WO 2005/019268 | 3/2005 |
| WO | WO 2005/053642 | 6/2005 |
| WO | WO 2005/062949 | 7/2005 |
| WO | WO 2005/063201 | 7/2005 |
| WO | WO 2005/110067 | 11/2005 |
| WO | WO 2005/120152 | 12/2005 |
| WO | WO 2005/121348 | 12/2005 |
| WO | WO 2006/016657 | 2/2006 |
| WO | WO 2006/123724 | 11/2006 |
| WO | WO 2007/043640 | 4/2007 |
| WO | WO 2007/076328 | 7/2007 |
| WO | WO 2007/080902 | 7/2007 |
| WO | WO 2007/086881 | 8/2007 |
| WO | WO 2007/099869 | 9/2007 |
| WO | WO 2007/132882 | 11/2007 |

OTHER PUBLICATIONS

Aizaki et al., "Characterization of the hepatitis C virus RNA replication complex associated with lipid rafts," Virology, 324:450-461 (2004).
Bae et al., "Cholesterol biosynthesis from lanosterol: development of a novel assay method and characterization of rat liver microsomal lanosterol delta 24-reductase," Biochem J., 326(Pt 2):609-16 (1997).
Balsano, "Recent advances in antiviral agents: established and innovative therapies for viral hepatitis," Mini Rev. Med. Chem., 8:307-318 (2008).
Bordier et al., "A Prenylation Inhibitor Prevents Production of Infectious Hepatitis Delta Virus Particles," J. Virol., 76:10465-10472 (2002).
Di Stasi et al., "DHCR24 gene expression is upregulated in melanoma metastases and associated to resistance to oxidative stress-induced apoptosis," Int. J. Cancer., 115(2):224-30 (2005).
Fujita et al., "Fungal Metabolites. Part 11. A Potent Immunosuppressive Activity Found in Isaria sinclairii Metabolite," J. Antibiot. (Tokyo), 47:208-215 (1994).
Futerman et al., "The ins and outs of sphingolipid synthesis," Trends in Cell Biology, 15(6):312-318 (2005).
Gao et al., "Interactions between Viral Nonstructural Proteins and Host Protein hVAP-33 Mediate the Formation of Hepatitis C Virus RNA Replication Complex on Lipid Raft," J. Virol., 78:3480-88 (2004).
Glue et al., "A Dose-Ranging Study of Pegylated Interferon Alfa-2b and Ribavirin in Chronic Hepatitis C," Hepatol., 32:647-653 (2000).
Guillas et al., "Human Homologues of LAG1 Reconstitute Acyl-CoA-dependent Ceramide Synthesis in Yeast," J. Biol. Chem., 278:37083-37091 (2003).
Leu et al., "Anti-HCV activities of selective polyunsaturated fatty acids," Biochem. Biophys. Res. Commun., 318:275-280 (2004).
Lohmann et al., "Replication of Subgenomic Hepatitis C Virus RNAs in a Hepatoma Cell Line," Science, 285:110-113 (1999).
Lucero et al., "Lipid rafts-protein association and the regulation of protein activity," Arch. Biochem. Biophys., 426:208-224 (2004).
Mahfoud et al., "Identification of a common sphingolipid-binding domain in Alzheimer, prion, and HIV-1 proteins," J. Biol. Chem., 277(13):11292-6 (2002).
Mandala et al., "Viridiofungins, Novel Inhibitors of Sphingolipid Synthesis," J. Antibiot. (Tokyo), 50:339-343 (1997).

Miyake et al., "Serine palmitoyltransferase is the primary target of a sphingosine-like immunosuppressant, ISP-1/myriocin," Biochem. Biophys. Res. Commun., 211:396-403 (1995).
Nehete et al., "A post-CD4-binding step involving interaction of the V3 region of viral gp120 with host cell surface glycosphingolipids is common to entry and infection by diverse HIV-1 strains," Antiviral Res., 56(3):233-51 (2002).
Ni and Wagman, "Progress and development of small molecule HCV antivirals,"Curr. Opin. Drug Discov. Devel., 7(4):446-459 (2004).
Onishi et al., "Antimicrobial Activity of Viridiofungins," J. Antibiot. (Tokyo), 50:334-338 (1997).
Reddy et al., "Efficacy and Safety of Pegylated (40-kd) Interferon α-2a Compared With Interferon α-2a in Noncirrhotic Patients With Chronic Hepatitis C," Hepatol., 33:433-438 (2001).
Riebeling et al., "Two Mammalian Longevity Assurance Gene (LAG1) Family Members, trh1 and trh4, Regulate Dihydroceramide Synthesis Using Different Fatty Acyl-CoA Donors," J. Biol. Chem., 278:43452-43459 (2003).
Rosenberg, "Recent Advances in the Molecular Biology of Hepatitis C Virus," J. Mol. Biol., 313:451-464 (2001).
Sakamoto et al., "Host sphingolipid biosynthesis as a target for hepatitis C virus therapy," Nat. Chem. Biol., 1(6):333-337 (2005).
Sakamoto et al., "Identification of a novel small molecule hepatitis C virus replication inhibitor that targets host sphingolipid biosynthesis," Hepatology, 42(4)(Suppl. 1) 535A:863 (2005).
Shi et al., "Hepatitis C virus RNA replication occurs on a detergent-resistant membrane that cofractionates with caveolin-2," J. Virol., 77(7):4160-8 (2003).
Simons and Ikonen, "Functional rafts in cell membranes," Nature, 387:569-572 (1997).
Takeda et al., "Influenza virus hemagglutinin concentrates in lipid raft microdomains for efficient viral fusion," Proc. Natl. Acad. Sci. USA, 100:14610-14617 (2003).
Umehara et al., "Serine palmitoyltransferase inhibitor suppresses HCV replication in a mouse model," Biochem. Biophys. Res. Commun., 346(1):67-73 (2006).
Worgall et al., "Ceramide Synthesis Correlates with the Post-transcriptional Regulation of the Sterol-Regulatory Element-Binding Protein," Arterioscler. Thromb. Vasc. Biol., 24:943-948 (2004).
Yamaoka et al., "Expression Cloning of a Human cDNA Restoring Sphingomyelin Synthesis and Cell Growth in Sphingomyelin Synthase-defective Lymphoid Cells," J. Biol. Chem., 279(18):18688-18693 (2004).
Ye et al., "Disruption of hepatitis C virus RNA replication through inhibition of host protein geranylgeranylation," Proc. Natl. Acad. Sci. U.S.A., 100(26):15865-70 (2003).
Zweerink et al., "Characterization of a Novel, Potent, and Specific Inhibitor of Serine Palmitoyltransferase," J. Biol. Chem., 267:25032-25038 (1992).
International Preliminary Report on Patentability for App. Ser. No. PCT/JP2007/060016, dated Dec. 10, 2008, 8 pages.
International Search Report for App. Ser. No. PCT/JP2007/060016, mailed Jun. 19, 2007, 2 pages.
USPTO Restriction Requirement in U.S. Appl. No. 11/659,779, dated Jun. 22, 2010, 12 pages.
Fish & Richardson P.C., Reply to Restriction Requirement dated Jun. 22, 2010 in U.S. Appl. No. 11/659,779, filed Jul. 14, 2010, 1 page.
USPTO Non-Final Office Action in U.S. Appl. No. 11/659,779, dated Sep. 27, 2010, 7 pages.
Fish & Richardson P.C., Amendment in Reply to Action dated Sep. 27, 2010 in U.S. Appl. No. 11/659,779, filed Feb. 25, 2011, 13 pages.
USPTO Non-Final Office Action in U.S. Appl. No. 11/659,779, dated May 13, 2011, 15 pages.
International Preliminary Report on Patentability for App. Ser. No. PCT/JP2005/014767, dated Feb. 20, 2007, 8 pages.
International Search Report for App. Ser. No. PCT/JP2005/014767, mailed Nov. 15, 2005, 3 pages.
European Search Report for App. Ser. No. EP 05 77 0415, dated Jun. 16, 2009, 3 pages.
International Search Report for App. Ser. No. PCT/JP2009/069934, dated Feb. 16, 2010, 5 pages.

(56) References Cited

OTHER PUBLICATIONS

Chevalier et al., "Inhibition of hepatitis C virus infection in cell culture by small interfering RNAs," *Mol. Ther.*, 15(8):1452-62 (2007).
Vlassov et al., "shRNAs targeting hepatitis C: effects of sequence and structural features, and comparison with siRNA," *Oligonucleotides*, 17(2):223-36 (2007).
European Search Report for App. Ser. No. EP 09 829 126.3, dated Aug. 22, 2012, 7 pages.
Choo et al., "Genetic organization and diversity of the hepatitis C virus," *Proc Natl Acad Sci U S A.*, 88(6):2451-5 (1991).
Fire et al., "Potent and specific genetic interference by double-stranded RNA in *Caenorhabditis elegans*," *Nature*, 391(6669):806-11 (1998).
Honda et al., "Stability of a stem-loop involving the initiator AUG controls the efficiency of internal initiation of translation on hepatitis C virus RNA," *RNA*, 2(10):955-68 (1996).
Honda et al., "A phylogenetically conserved stem-loop structure at the 5' border of the internal ribosome entry site of hepatitis C virus is required for cap-independent viral translation," *J Virol.*, 73(2):1165-74 (1999).
Ito et al., "The 3'-untranslated region of hepatitis C virus RNA enhances translation from an internal ribosomal entry site," *J Virol.*, 72(11):8789-96 (1998).
Kamoshita et al., "Genetic analysis of internal ribosomal entry site on hepatitis C virus RNA: implication for involvement of the highly ordered structure and cell type-specific transacting factors," *Virology.*, 233(1):9-18 (1997).
Kato et al., "Molecular cloning of the human hepatitis C virus genome from Japanese patients with non-A, non-B hepatitis," *Proc Natl Acad Sci U S A.*, 87(24):9524-8 (1990).
Mandala et al., "Isolation and characterization of novel inhibitors of sphingolipid synthesis: australifungin, viridiofungins, rustmicin, and khafrefungin," *Methods Enzymol.*, 311:335-348 (2000).
Miyakawa et al., "Classifying hepatitis B virus genotypes," *Intervirology*, 46:329-338 (2003).
Okamoto et al., "Nucleotide sequence of the genomic RNA of hepatitis C virus isolated from a human carrier: comparison with reported isolates for conserved and divergent regions," *J Gen Virol.*, 72(Pt 11):2697-704 (1991).
Okamoto et al., "Full-length sequence of a hepatitis C virus genome having poor homology to reported isolates: comparative study of four distinct genotypes," *Virology.*, 188(1):331-41 (1992).
Orito et al., "A case-control study for clinical and molecular biological differences between hepatitis B viruses of genotypes B and C. Japan HBV Genotype Research Group," *Hepatology*, 33(1):218-223 (2001).
Ozasa et al., "Influence of genotypes and precore mutations on fulminant or chronic outcome of acute hepatitis B virus infection," *Hepatology*, 44(2):326-334 (2006).
Sasano et al., "Sequence analysis of the IRES-Loop III region of hepatitis C virus," *Genome Inf. Ser.*, 9:395-6 (1998).
Sugiyama et al., "Influence of hepatitis B virus genotypes on the intra- and extracellular expression of viral DNA and antigens," *Hepatology*, 44(4):915-924 (2006).
Takamizawa et al., "Structure and organization of the hepatitis C virus genome isolated from human carriers," *J. Virol.*, 65(3):1105-13 (1991).
Tsukiyama-Kohara et al., "Internal ribosome entry site within hepatitis C virus RNA," *J Virol.*, 66(3):1476-83 (1992).
Watanabe et al., "Intracellular-diced dsRNA has enhanced efficacy for silencing HCV RNA and overcomes variation in the viral genotype," *Gene Ther.*, 13(11):883-92 (2006).
Watanabe et al., "Therapeutic application of RNA interference for hepatitis C virus," *Adv Drug Deliv Rev.*, 59(12):1263-76 (2007).
International Search Report for App. Ser. No. PCT/JP2009/061087, dated Jan. 30, 2009, 3 pages.
USPTO Restriction Requirement in U.S. Appl. No. 12/301,001, dated Aug. 16, 2011, 7 pages.
International Preliminary Report on Patentability for App. Ser. No. PCT/JP2009/069934, dated Jul. 5, 2011, 10 pages.
USPTO Interview Summary in U.S. Appl. No. 11/659,779, dated Jan. 11, 2012, 2 pages.
USPTO Interview Summary in U.S. Appl. No. 11/659,779, dated Jan. 17, 2012, 2 pages.
USPTO Notice of Allowance in U.S. Appl. No. 11/659,779, dated Jan. 24, 2012, 15 pages.
U.S. Appl. No. 12/301,001, filed Jun. 2, 2009, Kohara et al.
Gimenez-Barcons et al., "Endoribonuclease-prepared short interfering RNAs induce effective and specific inhibition of human immunodeficiency virus type 1 replication," *J. Virol.*, 81(19):10680-6 (2007).
Nishina et al., "Efficient in vivo delivery of siRNA to the liver by conjugation of alpha-tocopherol," *Mol. Ther.*, 16(4):734-40 (2008).
Scherr et al., "Inhibition of GM-CSF receptor function by stable RNA interference in a NOD/SCID mouse hematopoietic stem cell transplantation model," *Oligonucleotides*, 13(5):353-63 (2003).
Song et al., "RNA interference targeting Fas protects mice from fulminant hepatitis," *Nat. Med.*, 9(3):347-51 (2003).
Watanabe et al., "Liver target delivery of small interfering RNA to the HCV gene by lactosylated cationic liposome," *J. Hepatol.*, 47(6):744-50 (2007).
Wu et al., "Receptor-mediated in vitro gene transformation by a soluble DNA carrier system," *J. Biol. Chem.*, 262(10):4429-32 (1987).
U.S. Appl. No. 12/999,055, filed Mar. 15, 2011.
Amarzguioui et al., "Rational design and in vitro and in vivo delivery of Dicer substrate siRNA," *Nat Protoc.*, 1(2):508-517 (2006).
Matveeva et al., "Comparison of approaches for rational siRNA design leading to a new efficient and transparent method," *Nucleic Acids Res.*, 35(8):e63. Epub Apr. 10, 2007.
Dai 13 kai Nihon bunnsi seibutsu gakkai Nennkai/Dai 81 kai Nihon seikagakkai taikai goudoutaikai kouen youshisbu, Nov. 20, 2008: 2P-1426 (with English translation).

\* cited by examiner

SEQUENCE LISTING

<160> NUMBER OF SEQ ID NOS: 29

<210> SEQ ID NO 1
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 1
caucaugagc acaaauccua a                                          21

<210> SEQ ID NO 2
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 2
aggauuugug cucaugaugc a                                          21

<210> SEQ ID NO 3
<211> LENGTH: 21
<212> TYPE: RNA
<213> ORGANISM: Artificial
<220> FEATURE:

```
<223> OTHER INFORMATION: An artificially synthesized sequence for siRNA

<400> SEQUENCE: 3
guagaccgug caucaugagc a                                              21

<210> SEQ ID NO 4
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 4
cucaugaugc acggucuacg a                                              21

<210> SEQ ID NO 5
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 5
cguagaccgu gcaucaugag c                                              21

<210> SEQ ID NO 6
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 6
ucaugaugca cggucuacga g                                              21

<210> SEQ ID NO 7
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 7
gugcaucaug agcacaaauc c                                              21

<210> SEQ ID NO 8
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 8
auuugugcuc augaugcacg g                                              21

<210> SEQ ID NO 9
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 9
ggaggucucg uagaccgugc a                                              21
```

```
<210> SEQ ID NO 10
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 10
cacggucuac gagaccuccc g                                              21

<210> SEQ ID NO 11
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 11
aucaugagca caaauccuaa a                                              21

<210> SEQ ID NO 12
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 12
uaggauuugu gcucaugaug c                                              21

<210> SEQ ID NO 13
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 13
aaccaaacgu aacaccaacc g                                              21

<210> SEQ ID NO 14
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 14
guugguguua cguuugguuu u                                              21

<210> SEQ ID NO 15
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 15
accaaacgua acaccaaccg c                                              21

<210> SEQ ID NO 16
<211> LENGTH: 21
<212> TYPE: RNA
<213> ORGANISM: Artificial
<220> FEATURE:
<223> OTHER INFORMATION: An artificially synthesized sequence for siRNA
```

```
<400> SEQUENCE: 16 gguuggguguu acguuugguu u                                              21

<210> SEQ ID NO 17
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 17
agaaaaacca aacguaacac c                                               21

<210> SEQ ID NO 18
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 18
uguuacguuu gguuuucuu u                                                21

<210> SEQ ID NO 19
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 19
uccuaaaccc caaagaaaaa c                                               21

<210> SEQ ID NO 20
<211> LENGTH: 21
<212> TYPE: RNA
<213> ORGANISM: Artificial
<220> FEATURE:
<223> OTHER INFORMATION: An artificially synthesized sequence for siRNA

<400> SEQUENCE: 20
uuuucuuugg gguuuaggau u                                               21

<210> SEQ ID NO 21
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 21
agaggaagat agagaaagag                                                 20

<210> SEQ ID NO 22
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 22
ccctcgttgc catagagggg ccaa                                            24

<210> SEQ ID NO 23
<211> LENGTH: 20
```

```
<212> TYPE: DNA
<213> ORGANISM: Artificial
<220> FEATURE:
<223> OTHER INFORMATION: An artificially synthesized primer sequence

<400> SEQUENCE: 23
gataggttgt cgccttccac                                              20

<210> SEQ ID NO 24
<211> LENGTH: 26
<212> TYPE: DNA
<213> ORGANISM: Artificial
<220> FEATURE:
<223> OTHER INFORMATION: An artificially synthesized nucleotide sequence

<400> SEQUENCE: 24
gaggtctcgt agaccgtgca tcatga                                       26

<210> SEQ ID NO 25
<211> LENGTH: 50
<212> TYPE: DNA
<213> ORGANISM: Artificial
<220> FEATURE:
<223> OTHER INFORMATION: An artificially synthesized nucleotide sequence

<400> SEQUENCE: 25
gagtgccccg ggaggtctcg tagaccgtgc atcatgagca caaatcctaa              50

<210> SEQ ID NO 26
<211> LENGTH: 40
<212> TYPE: DNA
<213> ORGANISM: Artificial
<220> FEATURE:
<223> OTHER INFORMATION: An artificially synthesized nucleotide sequence

<400> SEQUENCE: 26
tggatcaacc cgctcaatgc ctggagattt gggcgtgccc                        40

<210> SEQ ID NO 27
<211> LENGTH: 40
<212> TYPE: DNA
<213> ORGANISM: Artificial
<220> FEATURE:
<223> OTHER INFORMATION: An artificially synthesized nucleotide sequence

<400> SEQUENCE: 27
ccgcgagact gctagccgag tagtgttggg tcgcgaaagg                        40

<210> SEQ ID NO 28
<211> LENGTH: 40
<212> TYPE: DNA
<213> ORGANISM: Artificial
<220> FEATURE:
<223> OTHER INFORMATION: An artificially synthesized nucleotide sequence

<400> SEQUENCE: 28
ccttgtggta ctgcctgata gggtgcttgc gagtgccccg                        40

<210> SEQ ID NO 29
<211> LENGTH: 77
<212> TYPE: DNA
```

```
<213> ORGANISM: Artificial
<220> FEATURE:
<223> OTHER INFORMATION: An artificially synthesized nucleotide sequence

<400> SEQUENCE: 29
ggaggtctcg tagaccgtgc atcatgagca caaatcctaa accccaaaga aaaaccaaac      60
gtaacaccaa ccgccgc                                                    77
```

OLIGORIBONUCLEOTIDE OR PEPTIDE NUCLEIC ACID CAPABLE OF INHIBITING ACTIVITY OF HEPATITIS C VIRUS

CROSS-REFERENCE TO RELATED APPLICATIONS

This application is the National Stage of International Application Serial No. PCT/JP2009/069934, filed on Nov. 26, 2009, which claims the benefit of Japanese Application Serial No. 2008-301764, filed on Nov. 26, 2008.

TECHNICAL FIELD

The present invention relates to oligonucleotides or peptide nucleic acids that inhibit the activity of hepatitis C virus, vectors that express the oligonucleotides, agents that comprise them as an active ingredient for treating hepatitis C, and methods for inhibiting the viral replication ability by binding the oligonucleotides or peptide nucleic acids to hepatitis C virus RNAs.

BACKGROUND ART

Hepatitis C virus (hereinafter referred to as "HCV") is a major causative virus of post-transfusion non-A, non-B hepatitis. A cDNA of its gene was cloned in 1989. To date, many studies have been conducted on HCV using cloned gene cDNAs. In particular, socially important results such as prevention of infection and establishment of diagnostic methods have been achieved. Thus, the incidence of post-transfusion HCV infection is almost eliminated at the present. However, the number of HCV-infected patients is estimated to account for several percentages of the world's total population.

The hepatitis caused by HCV infection tends to be chronic and persistent. This leads to chronic hepatitis, which is known to develop into cirrhosis and then liver cancer at a very high rate. Thus, reliable treatment of hepatitis after HCV infection is an essential task.

Interferon (IFN) therapy is generally performed as a method for treating chronic hepatitis C. However, there are problems with IFN therapy, such as only 30% efficacy rate, frequent induction of adverse effects including fever, and high drug prices. Studies have been conducted to assess the types of IFN, administration method and dose. Furthermore, the efficacy rate is expected to improve as a result of the development of consensus IFNs. Also, therapies that use a combination of an IFN with an antiviral agent such as Ribavirin are under trial. However, to date, such therapeutic methods have not become reliable.

On the other hand, recently, a method for suppressing target gene expression using a double-stranded RNA against a target gene was developed as a method for suppressing the expression of a specific gene in animal cells in vivo (Non-patent Document 1). This method is called "RNA interference (RNAi)", which is a phenomenon in which a double-stranded RNA (dsRNA) introduced into cells causes specific degradation of a cellular mRNA corresponding to the dsRNA sequence, and the expression of a protein encoded by the mRNA is blocked. RNAi is an effective method for assessing the function of a novel gene by inhibiting its gene expression, and it is widely used in functional analyses of genes of *C. elegans*, *Drosophila*, etc.

The internal ribosomal entry site (IRES) which contains a 5' untranslated region and a portion of the core region is known to play an important role in the translational initiation and protein synthesis of HCV (Non-patent Document 2). The IRES region which plays an important role in HCV replication has various higher-order structures such as a stem region which forms a stem loop. There are many reports on the 5' untranslated region, IRES, and stem region of HCV (Non-patent Documents 2 to 12). As described above, the IRES region is a gene region important for HCV replication, and its primary structure (nucleotide sequence) is well conserved among HCVs having different genotypes.

There are multiple HCVs with different genotypes. Such HCVs include, for example, HCJ6, HCJ8, HCV-1, HCV-BK, HCV-J, HCVSHIMO, JCH1, JCH3, JFH1, R24, R6, and S14J. An IRES region that exhibits a higher identity among the sequences of multiple HCVs with different genotypes is preferably targeted to cover the HCV RNAs of multiple HCVs with different genotypes. However, the conformation of the IRES region is complex because the region exerts its translational initiation function by its higher-order structure. Thus, it has been difficult to identify siRNA sequences that exhibit highly efficient RNAi activity using a conventional algorithm for identifying siRNA sequences.

The present inventors have identified and reported siE sequences that exhibit a highly efficient RNAi activity (Non-patent Document 13). However, there has been a need to identify siRNA sequences that have a more effective RNAi activity against hepatitis C virus RNAs.

PRIOR ART DOCUMENTS

Patent Documents

[Patent Document 1] WO2004/078974

Non-Patent Documents

[Non-patent Document 1] Fire, A. et al., nature (1998) 391, 806-811
[Non-patent Document 2] Tsukiyama-Kohara K. et al., J. Virology (1992) 66, 1476-1483
[Non-patent Document 3] Kato. N. et al., Proc. Natl. Acad. Sci. USA., 87, 9524-9528, (1990)
[Non-patent Document 4] Proc. Natl. Acad. Sci. USA., 88, 2451-2455, (1991)
[Non-patent Document 5] J. Viol., 65, 1105-1113, (1991)
[Non-patent Document 6] J. Gen. Viol., 72, 2697-2704, (1991)
[Non-patent Document 7] Virology, 188, 331-341, (1992)
[Non-patent Document 8] Honda Masao. et al., J. Virol., 73, 1165-1174, (1999)
[Non-patent Document 9] Honda Masao et al., RNA, 2(10), 955-968, (1996)
[Non-patent Document 10] Sasano T. et al., Genome Inf. Ser., 9, 395-396, (1998)
[Non-patent Document 11] Ito T et al., J. Virol., 72, 8789-8796, (1998)
[Non-patent Document 12] Kamoshita N et al., Virology., 233, 9-18, (1997)
[Non-patent Document 13] Watanabe, T. et al., Gene Therapy 13: 883-892 (2006)

DISCLOSURE OF THE INVENTION

Problems to be Solved by the Invention

The present invention was achieved in view of the above circumstances. An objective of the present invention is to provide oligoribonucleotides and peptide nucleic acids that inhibit the activity of hepatitis C virus, and whose RNAi activity is more effective than previously identified oligoribonucleotides, vectors that express these oligonucleotides, agents that comprise them as an active ingredient for treating hepatitis C, and methods for inhibiting the viral replication ability by binding the oligonucleotides or peptide nucleic acids to hepatitis C virus RNAs. Another objective of the present invention is to provide methods for designing siRNAs that exhibit a more effective RNAi activity.

Means for Solving the Problems

To achieve the above objectives, the present inventors focused on siE sequences that have been thought to show RNAi activity against HCV viral RNAs, and selected mainly the D5-50 and D5-197 regions present within the IRES region to carry on the analysis. As a result, the present inventors successfully identified siRNA sequences that exhibit a more effective RNAi activity against hepatitis C virus RNAs, and thus completed the present invention.

Furthermore, the present inventors assessed the HCV propagation-inhibiting effect in an in vivo system, and this showed that the siRNAs have a significant inhibitory effect on HCV propagation in the in vivo system.

Specifically, the present invention relates to the inventions of [1] to [16] below.
[1] An oligoribonucleotide comprising the nucleotide sequence of any one of SEQ ID NOs: 1 to 20.
[2] An oligoribonucleotide that hybridizes under a stringent condition to an HCV RNA region comprising a sequence complementary to the oligoribonucleotide of [1], or an HCV RNA region that hybridizes to the oligoribonucleotide under a stringent condition.
[3] An oligoribonucleotide that has a nucleotide sequence comprising 19 to 23 consecutive nucleotides in the nucleotide sequence of any one of SEQ ID NOs: 24 to 29.
[4] An oligoribonucleotide that hybridizes under a stringent condition to an HCV RNA region comprising a sequence complementary to the oligoribonucleotide of [3], or an HCV RNA region that hybridizes to the oligoribonucleotide under a stringent condition.
[5] A vector that expresses the oligoribonucleotide of any one of [1] to [4].
[6] An agent for treating hepatitis C, which comprises as an active ingredient the oligoribonucleotide or peptide nucleic acid of any one of [1] to [4] or the vector of [5].
[7] A method for inhibiting the replication ability of HCV by binding the oligoribonucleotide or peptide nucleic acid of any one of [1] to [4] to an HCV RNA.
[8] A method for designing an siRNA that has efficient RNAi activity against a target gene, which comprises the steps of:
(i) cleaving the RNA of a target gene or a fragment thereof with Dicer;
(ii) identifying the cleavage site in the RNA;
(iii) selecting a sequence that comprises 18 to 23 consecutive nucleotides comprising the cleavage site in the RNA; and
(iv) designing an siRNA comprising the nucleotide sequence selected in step (iii).
[9] The design method of [8], wherein the target gene is a gene of a host cell.
[10] The design method of [8], wherein the target gene is a gene of an animal cell.
[11] The design method of [8], wherein the target gene is a viral gene.
[12] The design method of [11], wherein the viral gene is an RNA virus gene.
[13] The design method of [11] or [12], wherein the RNA of a target gene or a fragment thereof comprises a sequence that has a higher-order structure and which is conserved at a frequency of 80% to 90% or more among strains.
[14] The design method of [13], wherein the sequence that has a higher-order structure and which is conserved at a frequency of 80% to 90% or more among strains in the RNA of a target gene or a fragment thereof is a sequence comprising an internal ribosome entry site (IRES region).
[15] The design method of [8], wherein the RNA sequence has 20 to 400 nucleotides.
[16] The design method of [11] or [12], wherein the virus is HCV, HIV, influenza virus, HBV, dengue virus, measles virus, Norovirus, SARS virus, Rubella virus, poliovirus, RS virus, Marburg virus, Ebola virus, Crimean-Congo hemorrhagic fever virus, yellow fever virus, dengue fever virus, hepatitis G virus, rabies virus, or human T-lymphotropic virus.

MODE FOR CARRYING OUT THE INVENTION

Figure 1:
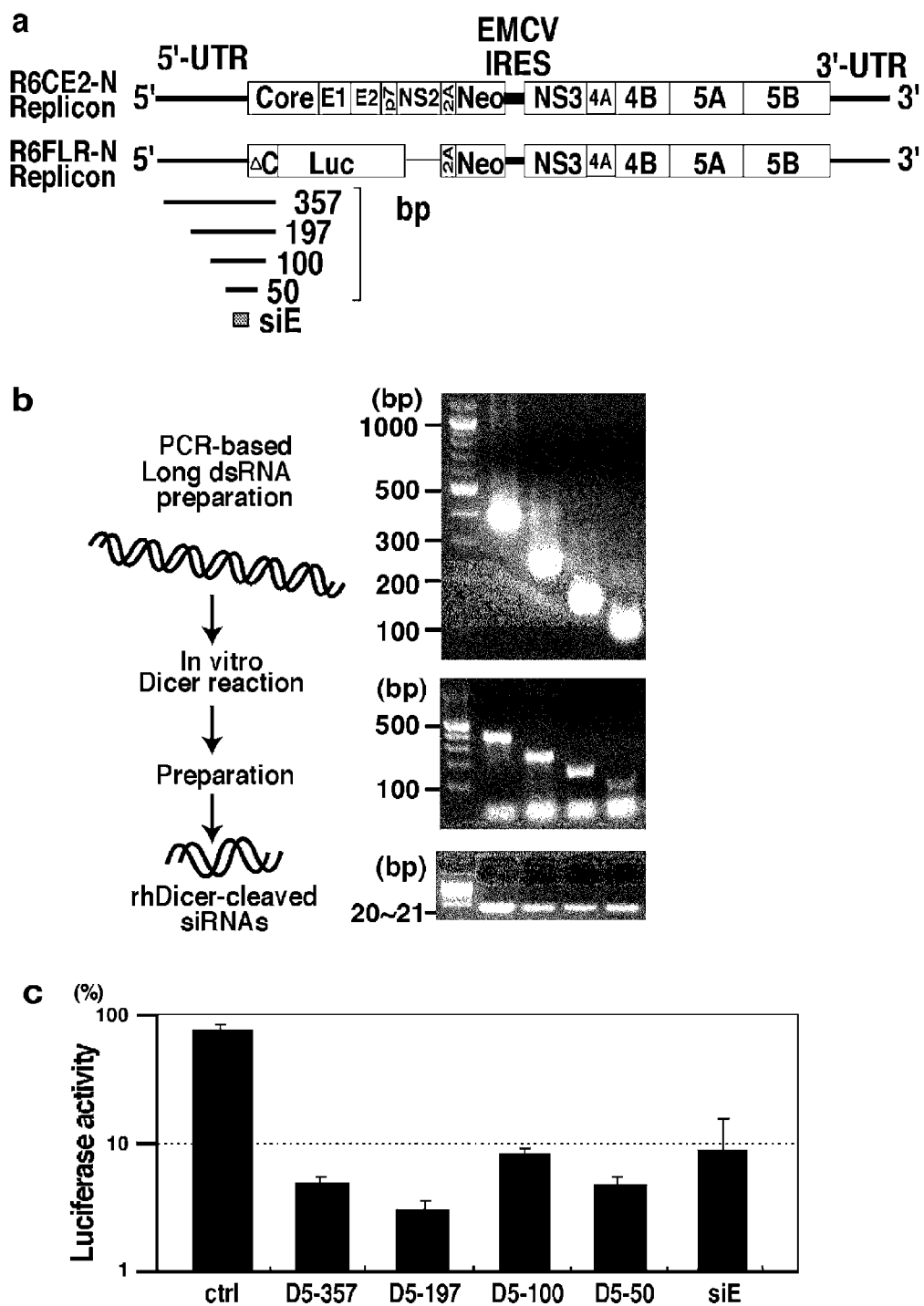
FIG. 1a shows the positions of long double-stranded RNAs in the HCV gene.
FIG. 1b shows assessment of siRNAs resulting from the Dicer protein-mediated cleavage of the long double-stranded RNAs by gel electrophoresis.
FIG. 1c shows the anti-HCV activities of the siRNAs prepared by cleaving the long double-stranded RNAs with the Dicer protein.
Figure 2:
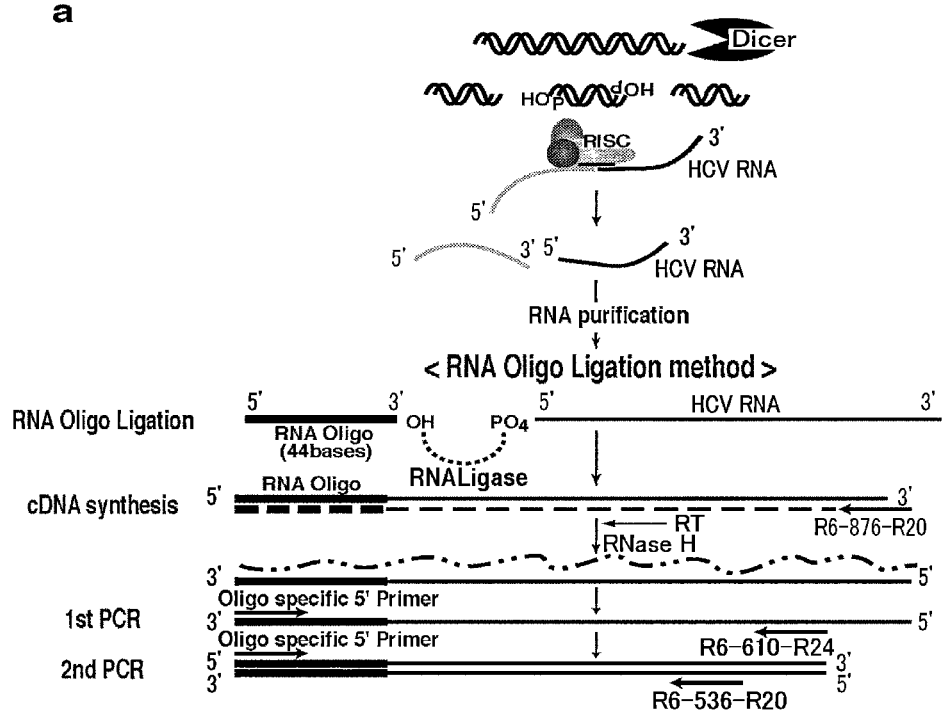
FIG. 2 shows a method for determining the nucleotide sequence of a cleavage end generated by siRNA-mediated cleavage of the HCV gene.
Figure 2:
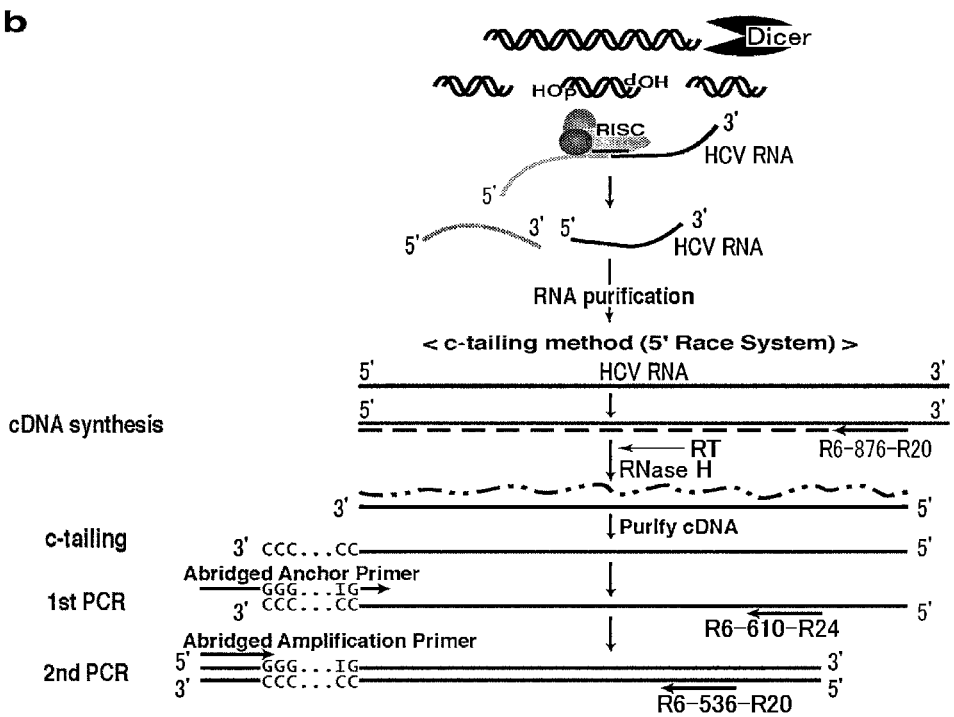

Oligo RNAs of the present invention that bind to HCV RNAs in a sequence-specific manner are oligonucleotides having ribose as the sugar, and the bases include thymine and those including other modified bases and such, in addition to adenine, guanine, cytosine, and uracil which are present in naturally-occurring RNAs. The oligo RNAs of the present invention are not particularly limited as long as they can bind to HCV RNAs in a sequence-specific manner; however, the oligo RNAs preferably inhibit the replication ability of HCV. The oligo RNAs capable of binding to HCV RNAs in a sequence-specific manner include, for example, oligo RNAs having a sequence complementary to the sequence of an HCV RNA, oligo RNAs having a sequence that exhibits high identity to a sequence complementary to the sequence of an HCV RNA, and oligo RNAs capable of hybridizing under stringent conditions to an RNA having the sequence of an HCV RNA. Without being bound by a particular theory, in a preferred embodiment of the present invention, the siRNAs are thought to hybridize to a target gene in cells and cleave the target gene with Dicer, and the target gene is cleaved into fragments of 19 to 23 nucleotides. Meanwhile, in another embodiment of the present invention, antisense nucleic acids are thought to induce IFN by hybridizing to a target gene, and degrade the target gene by activating RNase. Alternatively, it is thought that the antisense nucleic acids alter the structure of a target RNA by binding, and thereby inhibit translation. In the present invention, the HCV RNA sequence may be either a sequence of the HCV genomic RNA (negative strand), or the sequence of an mRNA transcribed from the genomic RNA (positive strand); however, the positive strand sequence is preferred.

Herein, "siRNA" refers to an oligo RNA that has a length of 19 to 23 nucleotides (19 to 23 bp). When an siRNA forms a double strand, it is possible for either one or both of the strands to have a protruding end.

Herein, "high sequence identity" refers to an identity of 70% or higher, preferably 80% or higher, and more preferably 90% or higher (for example, 95% or higher). The nucleotide sequence identity can be determined using the BLAST algorithm by Karlin and Altschul (Proc. Natl. Acad. Sci. USA 90:5873-5877, 1993) or the like. Programs called "BLASTN" and "BLASTX" have been developed based on this algorithm (Altschul et al., J. Mol. Biol. 215:403-410, 1990). When nucleotide sequences are analyzed using BLASTN based on BLAST, the parameters are set to, for example, score=100 and wordlength=12. Alternatively, when amino acid sequences are analyzed using BLASTX based on BLAST, the parameters are set to, for example, score=50 and wordlength=3. When BLAST and the Gapped BLAST program are used, the default parameters are used for each program. Specific procedures for these analytical methods are known (http://www.ncbi.nlm.nih.gov.).

Hybridization techniques are well known to those skilled in the art (for example, Sambrook, J. et al., Molecular Cloning 2nd ed., 9.47-9.58, Cold Spring Harbor Lab. press, 1989). Those skilled in the art can appropriately select stringent conditions. Stringent conditions include, for example, post-hybridization washing in 5×SSC and 0.1% SDS at 42° C., preferably 5×SSC and 0.1% SDS at 50° C., and more preferably 0.1×SSC and 0.1% SDS at 65° C. However, multiple factors such as temperature and salt concentration are thought to affect hybridization stringency, and those skilled in the art can suitably select these factors to accomplish similar stringencies.

The oligo RNAs of the present invention may be single-stranded or double-stranded, or may be formed from two or more multiple strands; however, double-stranded RNAs are preferable. The double strand may be formed from two independent strands, or may be formed in a self-complementary single-stranded RNA. In the latter case, a single molecule can form a stem-loop structure. When an oligo RNA is double-stranded, the double strand may be formed throughout the whole region. Alternatively, part of the region may form another structure such as single strand (for example, either one or both ends).

The length of an oligo RNA of the present invention is not limited, as long as it has the ability to bind to an HCV RNA in a sequence-specific manner. The length of an oligo RNA of the present invention is, for example, 5 to 1000 nucleotides (5 to 1000 bp in the case of double-stranded RNA), preferably 10 to 100 nucleotides (10 to 100 bp in the case of double-stranded RNA), more preferably 15 to 25 nucleotides (15 to 25 bp in the case of double-stranded RNA), and still more preferably 19 to 23 nucleotides (19 to 23 bp in the case of double-stranded RNA).

Preferred oligo RNAs of the present invention include oligo RNAs having the nucleotide sequence of any one of SEQ ID NOs: 1 to 20. Particularly preferred oligo RNAs include oligo RNAs having the nucleotide sequence of SEQ ID NOs: 11, 12, 19, or 20 (si197-#1 and si197-#6). Other preferred oligo RNAs of the present invention include oligo RNAs having a nucleotide sequence comprising 19 to 23 consecutive nucleotides in the nucleotide sequence of any one of SEQ ID NOs: 24 to 29.

The RNAs of the present invention can be expressed from an antisense-encoding DNA that encodes an antisense RNA targeting an arbitrary region of a target gene mRNA and a sense-encoding DNA that encodes a sense RNA targeting an arbitrary region of the target gene mRNA. Alternatively, dsRNA may be prepared from the antisense RNA and sense RNA. Combinations of antisense RNA and sense RNA include those of oligoribonucleotides having the nucleotide sequences of the following SEQ IDs: SEQ ID NOs: 1 and 2, SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 15 and 16, SEQ ID NOs: 17 and 18, and SEQ ID NOs: 19 and 20.

The double-stranded RNA portion (paired RNA) of a dsRNA is not necessarily completely paired, and may comprise an unpaired portion due to a mismatch (corresponding bases are not complementary), bulge (there is no corresponding base on one strand) or the like.

The end structure of an siRNA of the present invention may be blunt or sticky (protruding), as long as it can suppress the expression of an HCV viral gene through the RNAi effect. The sticky (protruding) end structures include not only 3' end-protruding structures but also 5' end-protruding structures as long as the RNAi effect is induced. The number of protruding nucleotides is not limited to two or three as already reported, and it may be any number of nucleotides as long as the RNAi effect can be induced. The number of nucleotides may range, for example, from one to eight, and preferably from two to four. Since the protruding sequence portion exhibits low specificity to the transcript of an HCV viral gene, the sequence is not necessarily complementary (antisense) or identical (sense) to the sequence of the target HCV viral gene transcript.

Other preferred oligo RNAs of the present invention include, for example, oligo RNAs that hybridize under stringent conditions to an HCV RNA region having a sequence complementary to an oligo RNA having the nucleotide sequence of any one of SEQ ID NOs: 1 to 20 mentioned above, or to an HCV RNA region that hybridizes under stringent conditions to the oligo RNA, and oligo RNAs that hybridize under stringent conditions to an HCV RNA region having a sequence complementary to an oligo RNA having the nucleotide sequence of 19 to 23 consecutive nucleotides in the nucleotide sequence of any one of SEQ ID NOs: 24 to 29 mentioned above, or to an HCV RNA region that hybridizes under stringent conditions to the oligoribonucleotide. Those skilled in the art can readily determine HCV RNA regions that hybridize under stringent conditions to these oligo RNAs for any HCV type. Such oligo RNAs include, for example, an oligo RNA that comprises a nucleotide sequence with deletion, substitution, or addition of seven nucleotides or less, preferably five nucleotides or less, and more preferably three nucleotides or less in the nucleotide sequence of any one of SEQ ID NOs: 1 to 20 mentioned above, or a nucleotide sequence comprising 19 to 23 consecutive nucleotides in the nucleotide sequence of any one of SEQ ID NOs: 24 to 29 mentioned above, and which can inhibit HCV replication by hybridizing to an HCV RNA.

Meanwhile, preferable peptide nucleic acids that can be used in the present invention include those having a nucleotide sequence corresponding to the sequence of a preferably usable oligo RNA in the present invention.

The HCV RNA is composed of the 5'-side untranslated region of about 340 nucleotides (5' untranslated region), open reading frame (ORF) of about 9,400 nucleotides, and 3'-side untranslated region of about 50 nucleotides (3' untranslated region). In this RNA sequence, there is no particular limitation on the site targeted by an oligo RNA of the present invention, and the oligo RNA may target any site. However, the site is preferably positioned between the 5' untranslated region and the 5'-end region of ORF, or at the 3' untranslated region, and more preferably at the 5' untranslated region.

Figure 7:
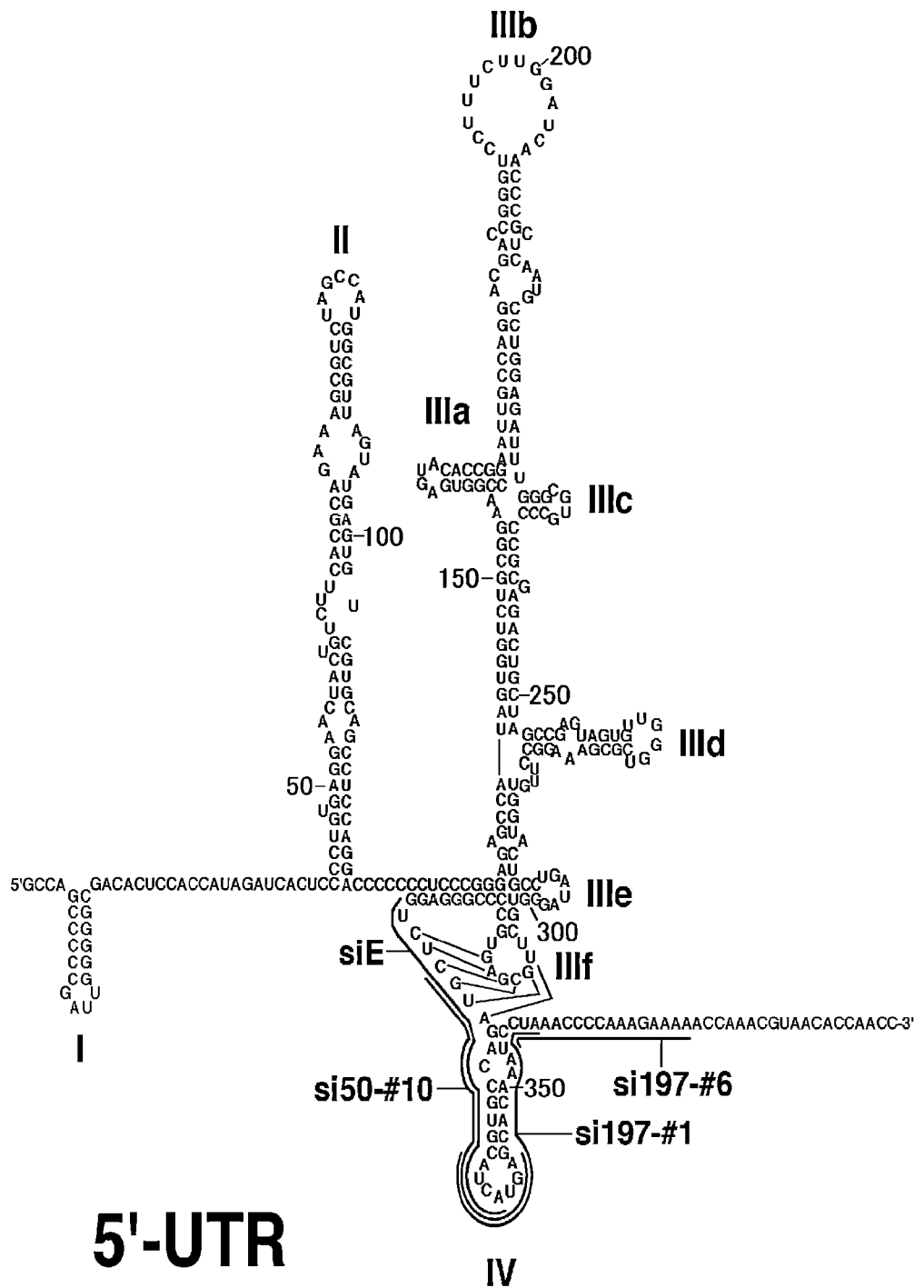
FIG. 7 shows the secondary structure of the 5' untranslated region (5'-UTR) of HCV. It shows a complex higher-order structure.

The 5' untranslated region of HCV RNA contains an internal ribosomal entry site (IRES), a stem region that forms a stem loop, etc. There have been many previous reports on the 5' untranslated region, IRES, and stem region of HCV (Kato N. et al., Proc. Natl. Acad. Sci. USA., 87, 9524-9528, (1990); Proc. Natl. Acad. Sci. USA., 88, 2451-2455, (1991); J. Viol., 65, 1105-1113, (1991); J. Gen. Viol., 72, 2697-2704, (1991); Virology, 188, 331-341, (1992); Tsukiyama, Kohara, et al., J. Virol., 66, 1476-1483, (1992); Honda Masao et al., J. Virol., 73, 1165-1174, (1999); Honda Masao et al., RNA, 2 (10), 955-968, (1996); Sasano T. et al., Genome Inf. Ser., 9, 395-396, (1998); Ito T et al., J. Virol., 72, 8789-8796, (1998); Kamoshita N et al., Virology., 233, 9-18, (1997)). FIG. 7 shows a general secondary structure of the 5' untranslated region of HCV RNA.

Meanwhile, there are multiple types of HCV having different genotypes. Such HCVs include, for example, HCJ6, HCJ8, HCV-1, HCV-BK, HCV-J, JCH1, JCH3, JFH1, R24, R6, S14J, pH77J6S (GenBank Accession no. AF177039), HCJ6CH, and 2b_AB030907. In order to cover such multiple HCV RNAs having different genotypes, it is preferable to target a region that has high identity among the gene sequences of HCV types having different genotypes. Herein, the "region having high identity among multiple HCV gene sequences having different genotypes" refers to a region exhibiting an RNA sequence identity of 80% or higher, preferably 90% or higher, and more preferably 95% or higher among multiple HCV types. Such regions preferably have ten nucleotides or more in length, more preferably 15 nucleotides or more in length, and still more preferably 20 nucleotides or more in length. Herein, "multiple HCV types" typically means three or more HCV types, preferably five or more HCV types, and more preferably ten or more HCV types. The identity of gene sequences can be calculated by comparing multiple gene sequences of interest using the above-described algorithms or such.

There is no particular limitation on the oligoribonucleotides used in the present invention. In addition to those having an ordinary non-modified RNA structure, modified RNAs in which a phosphodiester moiety or sugar moiety is modified, and such can be used. Furthermore, the oligo RNAs of the present invention may partially contain a molecule other than ribonucleotide such as deoxyribonucleotide.

Furthermore, in the present invention, peptide nucleic acids (PNAs) or the like may be used instead of the oligo RNAs. PNA is a technique well known to those skilled in the art (Nielsen Peter E., Methods in Molecular Biology, 208, 3-26, (2002); Braasch Dwaine A et al., Biochemistry, 41 (14), 4503-4510, (2002); Koppelhus Uffe et al., Antisense Drug Technology, 359-374, (2001); Nielsen Peter E., Methods in Enzymology, 340, 329-340, (2001)). Similar to the above oligo RNAs, one can produce peptide nucleic acids that can bind to an HCV RNA in a sequence-specific manner. The preferred length of a peptide nucleic acid of the present invention is, for example, 5 to 1000 bases (5 to 1000 bp in the case of a double-stranded peptide nucleic acid), preferably 10 to 100 bases (10 to 100 bp in the case of a double-stranded peptide nucleic acid), more preferably 15 to 25 bases (15 to 25 bp in the case of a double-stranded peptide nucleic acid), and still more preferably 19 to 23 bases (19 to 23 bp in the case of a double-stranded peptide nucleic acid).

The oligo RNAs or peptide nucleic acids of the present invention can be produced by methods known to those skilled in the art.

To express the oligo RNAs of the present invention continuously, vectors that express the oligo RNAs of the present invention may be prepared. Such vectors can be prepared by methods known to those skilled in the art, for example, by inserting a gene encoding an oligo RNA of the present invention into a known vector such as those described in Nature Biotech (2002) 19, 497-500. Preferred promoters for expression of oligo RNAs of the present invention include, but are not particularly limited to, the T7 promoter, tRNA promoter, and U6 promoter.

An siRNA of the present invention can be expressed in cells using a DNA encoding the above antisense RNA strand (hereinafter referred to as "antisense-encoding DNA") and a DNA encoding the above sense RNA strand (hereinafter referred to as "sense-encoding DNA") (hereinafter, the antisense-encoding DNA and sense-encoding DNA are simply referred to as "DNA of the present invention"). The "antisense-encoding DNA" and "sense-encoding DNA" can be integrated as they are introduced into the chromosome of cells together with a promoter to express the antisense and sense RNAs in the cells and produce an siRNA. However, the above siRNA expression system is preferably carried by a vector to achieve efficient intracellular introduction or such. The "vector" that can be used herein may be selected depending on the type of cells to be used for introduction, etc. For example, when the cells are mammalian cells, examples of the vector include, but are not limited to, viral vectors such as retroviral vectors, adenoviral vectors, adeno-associated virus vectors, vaccinia virus vectors, lentivirus vectors, herpes virus vectors, alpha-virus vectors, EB virus vectors, papilloma virus vectors, and foamy virus vectors, and non-viral vectors such as cationic liposomes, ligand/DNA complexes, and gene guns (Y. Niitsu et al., Molecular Medicine 35: 1385-1395 (1998)). Alternatively, instead of viral vectors, dumbbell DNAs (Zanta M. A. et al., Gene delivery: a single nuclear localization signal peptide is sufficient to carry DNA to the cell nucleus. Proc Natl Acad Sci USA. 1999 Jan. 5; 96 (1):91-6), modified DNAs with nuclease resistance, and naked plasmids can also be preferably used (Liu F, Huang L. Improving plasmid DNA-mediated liver gene transfer by prolonging its retention in the hepatic vasculature. J. Gene Med. 2001 November-December; 3 (6):569-76).

When a DNA encoding an siRNA of the present invention is carried by a vector or such, the antisense and sense RNA stands are expressed from the same vector, or they are individually expressed from separate vectors. For example, when the antisense and sense RNA strands are expressed from the same vector, the construct can be prepared by separately constructing antisense RNA and sense RNA expression cassettes in which a promoter such as the polIII system that allows expression of a short RNA, is linked upstream of the antisense-encoding DNA and sense-encoding DNA, respectively, and then inserting these cassettes into a vector in the same or opposite directions. Alternatively, the expression system may be constructed such that the antisense-encoding DNA and sense-encoding DNA are paired and placed on separate strands in the opposite directions. This construct comprises a double-stranded DNA (siRNA-encoding DNA) in which the antisense RNA-encoding strand and sense RNA-encoding strand are paired with each other, and promoters are placed at both ends thereof in the opposite directions such that the antisense RNA and sense RNA can be expressed from each strand. In this case, it is preferable to place a terminator at the 3' end of each strand (antisense RNA-encoding strand and sense RNA-encoding strand) to avoid addition of extra sequences downstream of the sense RNA and antisense RNA. A sequence of four or more consecutive adenine (A) nucleotides or the like may be used as the terminator. Furthermore, the types of the two promoters are preferably different in this palindromic-type expression system.

For the DNA encoding an siRNA of the present invention to be inserted into a vector, one can use a construct that has an appropriate sequence (an intron sequence is preferred) as an insert between the inverted repeats of a target sequence so as to form a double-stranded RNA having a hairpin structure (self-complementary "hairpin" RNA (hpRNA)) (Smith, N. A. et al., Nature, 407:319, 2000; Wesley, S. V. et al., Plant J. 27:581, 2001; Piccin, A. et al., Nucleic Acids Res. 29:E55, 2001).

Meanwhile, when the antisense RNA and sense RNA are expressed from separate vectors, the constructs can be prepared, for example, by separately constructing antisense RNA expression cassette and sense RNA expression cassette in which a promoter such as the polIII system that allows expression of a short RNA, is linked upstream of the antisense-encoding DNA and sense-encoding DNA, respectively, and then inserting these cassettes into separate vectors.

That is, the "DNA encoding an siRNA (double-stranded RNA)" of the present invention may be a single DNA encoding the two strands of an siRNA, or a combination of two DNAs respectively encoding the two strands of an siRNA. Furthermore, the "vectors having a DNA encoding an siRNA (double-stranded RNA) as an insert" may be a single vector that expresses the two strands of an siRNA as two transcripts or a single transcript, or two vectors that respectively express the two strands of an siRNA.

A DNA used for RNAi does not necessarily match its target gene perfectly; however, it has a sequence identity of at least 70% or higher, preferably 80% or higher, more preferably 90% or higher, and still more preferably 95% or higher (for example, 96%, 97%, 98%, 99% or higher). The nucleotide sequence identity can be determined using the BLAST algorithm mentioned above.

Since the oligo RNAs of the present invention can inhibit HCV replication and suppress HCV propagation, they are useful as agents for treating hepatitis C. By providing an oligoribonucleotide or peptide nucleic acid that targets multiple types of HCVs, patients can be treated without identifying the type of infecting virus in the clinical setting. This is preferable as there is no need to mix and use multiple types of oligoribonucleotides or peptide nucleic acids.

When used for therapies, the oligoribonucleotide or peptide nucleic acid may be administered in a form that functions as it is in cells. In this case, the most suitable length of oligo RNA or peptide nucleic acid is about 19 to 23 nucleotides. Alternatively, the oligoribonucleotide or peptide nucleic acid may be administered in a form that functions after being processed in cells. In this case, it is possible to administer an oligo RNA or peptide nucleic acid that has a longer sequence comprising a sequence of interest. A double-stranded RNA (dsRNA) incorporated into cells is degraded into siRNAs (short-interfering RNAs) of about 21mer by an enzyme called Dicer. The siRNAs form a complex called RNA-induced silencing complex (RISC), and it destroys RNAs transcribed from the genome that have a specific nucleotide sequence (Bernstein, E. et al., Nature, 409:363-366, 2001; Hammond, S. M. et al., Nature, 404:293-296, 2000). Alternatively, it is possible to use an siRNA prepared in advance in vitro utilizing a commercially available Dicer.

Various methods can be used to deliver siRNAs to cells, cell cultures, tissues, or cell populations such as embryos. For example, RNAs can be introduced directly into cells. Various physical methods such as administration by microinjection are generally used in such cases. Other cellular delivery methods include cell membrane permeabilization and electroporation, liposome-mediated transfection, and transfection using chemical substances such as calcium phosphate, which are carried out in the presence of siRNAs. Various established gene therapy techniques may be used to introduce siRNAs into cells. Viral constructs are introduced into virions to achieve, for example, efficient introduction of expression constructs into cells and transcription of RNAs encoded by the constructs.

As necessary, a pharmaceutically acceptable excipient, isotonizing agent, solubilizing agent, stabilizer, preservative, pain killer, or the like may be added to agents for treating hepatitis C that comprise an oligo RNA or peptide nucleic acid of the present invention as an active ingredient, and thus pharmaceutical compositions such as tablets, powders, granules, capsules, liposome capsules, injectable solutions, liquid preparations, nasal drops, and such can be prepared. Furthermore, they may be made into freeze-dried agents. They may be prepared by conventional methods. Alternatively, it is possible to administer vectors that express an oligo RNA of the present invention.

There is no particular limitation on the route of administration for an oligo RNA or peptide nucleic acid of the present invention. However, preferably, it is directly applied to the affected area of a patient, or applied to a patient by administration into blood vessels or the like so that it can eventually reach the affected area. Furthermore, encapsulating materials that enhance the durability or membrane permeability can also be used. Such materials include, for example, liposomes, poly-L-lysine, lipids, cholesterols, lipofectin, and derivatives thereof.

The dosage of an oligo RNA or peptide nucleic acid of the present invention may be appropriately adjusted to a preferred amount depending on the patient's conditions. It may be administered, for example, within the range of 0.001 to 100 mg/kg, preferably 0.1 to 10 mg/kg; however, the dosage is not particularly limited thereto.

The present invention also provides methods for inhibiting the replication ability of HCV by binding the above oligo RNA or peptide nucleic acid of the present invention to an HCV RNA. The methods of the present invention comprise contacting an oligo RNA or peptide nucleic acid of the present invention in vivo or in vitro with a sample containing or suspected to contain an HCV. Whether the replication ability of HCV is inhibited can be assessed by methods conventionally used in the art.

The present application further discloses methods that allow efficient selection and design of an siRNA sequence that has strong RNAi activity against a target gene. Various algorithms for siRNA design methods have been known, and various siRNAs have been designed using these algorithms. For example, it is known to cleave a target RNA with Dicer and use the resulting sequences as siRNAs. However, it cannot be said that such siRNAs identified by the above methods have significantly high RNAi activity, and the proportion of siRNAs having high activity is small.

The present inventors discovered that rather than using the sequences excised with Dicer as a basis, siRNAs having high RNAi activity can be designed more efficiently than ever before by identifying Dicer cleavage sites in a target RNA sequence; selecting nucleotide sequences of 19 to 23 residues from the target RNA that contain the specific sites; and selecting siRNA sequences based on the above nucleotide sequences. Furthermore, the design method of the present invention enables design of siRNAs having an activity stronger than ever before.

In the design method of the present invention, there is no particular limitation on the length of a target RNA to be cleaved with Dicer; however, the preferred length is 20 to 400 nucleotides.

The present inventors found that when a target RNA is cleaved with Dicer, the cleavage sites vary even in the same sequence depending on the length of the target RNA. As described in the Examples herein, when the target is the HCV IRES region, it is preferred that siRNAs are designed based on sequences containing the Dicer cleavage sites of a target RNA whose length is about 50 to 200 nucleotides.

When siRNAs are designed by the method of the present invention, a cleavage site for the corresponding target gene is preferably located around the center of a designed siRNA sequence. Specifically, it is preferred that there are 5 to 12 nucleotides on the 5' or 3' side of the cleavage site as the center, and it is more preferred that there are 8 to 12 nucleotides on the 5' or 3' side of the cleavage site.

When the target gene is a host cell gene or animal cell gene in the design method of the present invention, for example, siRNAs against the target gene can be designed by cleaving its mRNA or a fragment thereof with Dicer, and identifying the cleavage sites.

In the design method of the present invention, when the target gene is a viral gene such as an RNA virus gene, for example, siRNAs against the target viral gene can be designed by cleaving with Dicer a target gene-derived RNA fragment containing a sequence that has a higher-order structure, and which is conserved at a frequency of 80% or higher, preferably 90% or higher among strains, and derived from the RNA sequence corresponding to the viral gene; and identifying the cleavage sites.

Such sequences having a higher-order structure and conserved at a frequency of 80% or higher, preferably 90% or higher among strains include, for example, the internal ribosome entry site (IRES) sequence of an RNA virus such as HCV, the best conserved regions of HIV (Yuki Naito et al., Retrovirology, 2007, 4:80), and the 5'-end highly conserved region of influenza virus.

In the design method of the present invention, the target viruses are not particularly limited as long as they have a nucleotide sequence that has a higher-order structure and which is conserved at a frequency of 80% or higher among strains; however, the viruses preferably include DNA viruses (Poxyiridae, Herpesviridae, Adenoviridae, Papovaviridae, Parvoviridae, and Hepadnaviridae) and RNA viruses (Arenaviridae, Orthomyxoviridae, Caliciviridae, Coronaviridae, Togaviridae, Nodaviridae, Paramyxoviridae, Picornaviridae, Filoviridae, Bunyaviridae, Rhabdoviridae, Reoviridae, and Retroviridae). Specifically, the above target viruses include HCV, HIV, influenza virus, HBV, dengue virus, measles virus, Norovirus, SARS virus, Rubella virus, poliovirus, RS virus, Marburg virus, Ebola virus, Crimean-Congo hemorrhagic fever virus, yellow fever virus, dengue fever virus, hepatitis G virus, rabies virus, and human T-lymphotropic virus. Preferred viruses are HCV, HIV, influenza virus, HBV, dengue virus, and measles virus, and a more preferred virus is HCV.

All prior art documents cited in the specification are incorporated herein by reference.

EXAMPLES

Hereinbelow, the present invention will be more specifically described with reference to the Examples, but it is not to be construed as being limited thereto.

Example 1

Analysis of Sites Cleaved by Diced siRNAs in HCV Replicon RNAs

Transfection of Diced siRNAs
<Transfection Method Using Lipofectamine 2000>

On the day before the start of the experiment, div. bla n3 cells carrying an HCV replicon were plated in 6-well plates (BECTON DICKINSON, cat. #353046) at 250,000 cells/2 ml/well using DMEM+GlutaMAX-I (Invitrogen, cat. #10569-044) supplemented with 5% inactivated FCS (Invitrogen, cat. #26140-079).

On the first day of the experiment, div. bla n3 cells were transfected with a diced siRNA (D5-50 or D5-197) (FIG. 3) at a final concentration of 30 nM using the Lipofectamine 2000 Reagent (Invitrogen, cat. #11668-019). This method (according to the product manual) is described below.

The diced siRNA for transfection was diluted to 300 nM with OPTI-MEM I (Invitrogen, cat. #22600-050) containing 0.23% $NaHCO_3$. Meanwhile, Lipofectamine 2000 was diluted to 3% with 0.23% $NaHCO_3$/OPTI-MEM I, and this was gently mixed and allowed to stand at room temperature for five minutes. An equal volume of the 300 nM diced siRNA solution and 3% Lipofectamine 2000 solution were mixed, and this was allowed to stand at room temperature for 20 minutes. The siRNA/Lipofectamine mixed solution was added at 500 µl/well to div. bla n3 prepared on the previous day in 6-well plates, and this was mixed. The cells were incubated at 37° C. under 5% $CO_2$ in an incubator, and then the sample was collected six hours after the start of transfection.

<Transfection Method Using Lipofectamine RNAiMAX>

On the first day of the experiment, div. bla n3 cells were transfected with the siRNA (siE-R5) (FIG. 3) at a final concentration of 30 nM using the Lipofectamine RNAiMAX Reagent (Invitrogen, cat. #13778-015). This method (according to the product manual) is described below.

The siRNA for transfection (siE-R5) was diluted to 180 nM with 0.23% $NaHCO_3$/OPTI-MEM I. The diluted siRNA was aliquoted at 500 µl/well into 6-well plates, and then Lipofectamine RNAiMAX Reagent was added thereto at 2.5 µl/well. This was mixed gently, and then allowed to stand at room temperature for 20 minutes. div. bla n3 cells were plated at 380,000 cells/2.5 ml/well in 6-well plates containing the siRNA/Lipofectamine mixed solution. DMEM+ GlutaMAX-I supplemented with 10% inactivated FCS was used for plating. The cells were incubated at 37° C. under 5% $CO_2$ in an incubator, and the sample was collected six hours after the start of transfection.

RNA Extraction Method

Six hours after the start of transfection, the medium was removed by aspiration, and 5 M GTC solution (5 M guanidine thiocyanate (Fluka, cat. #50980), 37.5 mM sodium citrate (pH 7.0) (WAKO, cat. #191-01785), and 0.75% sarkosyl (N-lauroylsarcosine sodium salt; nacalai tesque, cat. #201-17)) containing 1.4% 2-Mercaptoethanol (nacalai tesque, cat. #21438-82) was added at 1,300 μl per well. The cells were completely lysed by pipetting.

27 μl of 3 M sodium acetate (pH 5.2) (Wako, cat. #198-01055) was added to 400 μl of the 5 M GTC cell lysis solution, and this was mixed. Then, 400 μl of TE-saturated phenol (Wako, cat. #160-12725) was added thereto, and this was gently mixed for one minute, and then allowed to stand on ice for 15 minutes. Next, 90 μl of chloroform/isoamyl alcohol (49:1) (chloroform, Wako, cat. #038-02606; isoamyl alcohol, Wako, cat. #017-03676) solution was added thereto, and this was gently mixed for one minute, and then allowed to stand on ice for 15 minutes. The mixture was centrifuged at 15,000 rpm and 4° C. for 20 minutes, and the upper layer was transferred into a fresh tube. An equal volume of 2-propanol (Wako, 166-04836) was added thereto, and this was mixed. This was cooled at −20° C. for two hours, and centrifuged at 15,000 rpm and 4° C. for ten minutes to precipitate RNA. The RNA pellet was washed with 80% ethanol (Wako, cat.#057-00451) cooled at −20° C., and then this was centrifuged at 15,000 rpm and 4° C. for five minutes. This washing treatment was repeated four times. The pellet was air-dried for several seconds, and dissolved in 11 μl of RNA/DW (10 mM DTT (Fluka, cat. #43815), 200 U/ml Ribonuclease Inhibitor (TaKaRa, cat. #2310A)). The RNA concentration was determined.

Identification Method 1: Identification of Cleavage Sites in HCV replicon RNAs Using the Adaptor Method The GeneRacer Kit (Invitrogen, cat. #L1502-01) was partially used (according to the protocols described in "RNA Oligo addition" and later in the product manual).

Addition of RNA Oligo to HCV RNA Samples

The total volume of a sample containing 1 to 5 μg of RNA was adjusted to 7 μl, and this was added to a tube containing freeze-dried GeneRacer RNA Oligo. The sample was pipetted several times to be mixed with the RNA Oligo. This was incubated at 65° C. for five minutes, and then rapidly cooled on ice. 1 μl each of the ligation reagent (10× ligase buffer, 10 mM ATP, RNase OUT, and T4 RNA ligase) was added thereto, and the mixture was incubated at 37° C. for one hour. 90 μl of Nuclease-Free Water (Ambion, cat. #9932) was added thereto, and then this was mixed with an equal volume of phenol/chloroform solution. The mixture was centrifuged, and the supernatant was transferred into a fresh tube. 2 μl of 10 mg/ml mussel glycogen and 10 μl of 3 M sodium acetate (pH 5.2) were added thereto and this was mixed. Then, 220 μl of ethanol was added thereto, and this was mixed. The mixture was cooled at −80° C. for 15 minutes, and then centrifuged at 15,000 rpm and 4° C. for 20 minutes. The pellet was washed with 70% ethanol, and briefly air-dried, and then dissolved in 9 μl of Nuclease-Free Water.

Reverse Transcription of HCV RNAs

The SuperScript III RT Module attached to the GeneRacer Kit was used in this experiment.

1 μl of 100 μM Gene Specific Reverse Primer (R6-876-R20) (SEQ ID NO: 21; see Table 1) was combined with the RNA Oligo-added RNA, and 1 μl of 10 mM dNTP mixture solution (GE Healthcare, cat. #28-4065-51) was added thereto. The mixture was heated at 70° C. for three minutes, and then rapidly cooled on ice. 2 μl of 10×RT Buffer, 4 μl of 25 mM $MgCl_2$, 2 μl of 0.1 M DTT, and 1 μl of RNase OUT were added thereto, and this was mixed by pipetting. After two minutes of incubation at 25° C., 1 μl of SuperScript III RT was added thereto, and this was mixed. Then, this was incubated at 25° C. for ten minutes, at 50° C. for 30 minutes, at 55° C. for 30 minutes, and at 85° C. for 5 minutes, and then allowed to stand on ice. 1 μl of RNase H was added thereto, and this was incubated at 37° C. for 20 minutes. A 2-μl aliquot of this reaction mixture was used as a template for the first-round PCR.

TABLE 1

| PRIMER NAME | PRIMER SEQUENCE (5' to 3') | START POINT |
|---|---|---|
| R6-876-R20 | AGAGGAAGATAGAGAAAGAG (SEQ ID NO: 21) | 876 |
| R6-610-R24 | CCCTCGTTGCCATAGAGGGGCCAA (SEQ ID NO: 22) | 610 |
| R6-536-R20 | GATAGGTTGTCGCCTTCCAC (SEQ ID NO: 23) | 536 |

First-Round PCR of the Oligo-Added HCV RNA

Phusion DNA Polymerase (Finnzymes, cat. #F-530L) was used.

2 μl of a template cDNA was combined with 28.2 μl of $ddH_2O$, 10 μl of 5× Phusion HF Buffer, 1 μl of 10 mM dNTPs, 5 μl of 10 μM GeneRacer 5' Primer, 3.3 μl of 10 μM R6 610-R24 reverse primer (SEQ ID NO: 22; see Table 1), and 0.5 μl of Phusion DNA Polymerase. PCR was carried out in a total volume of 50 μl. The PCR program was: 98° C. for two minutes; 20 cycles of 98° C. for ten seconds and 72° C. for 30 seconds; heating at 72° C. for five minutes, and rapid cooling to 4° C. The first-round PCR product was used as a template for the second-round PCR.

Second-Round PCR of the Oligo-Added HCV RNA

AmpliTaq Gold with GeneAmp (Applied Biosystems, cat. #N888-0249) was used.

5 μl of the first-round PCR DNA sample was combined with 24.2 μl of $ddH_2O$, 5 μl of 10×PCR Buffer II, 6 μl of 25 mM $MgCl_2$, 1 μl of 10 mM dNTPs, 5 μl of 10 μM GeneRacer 5' Primer, 3.3 μl of 10 μM R6 536-R20 reverse primer (SEQ ID NO: 23; see Table 1), and 0.5 μl of Taq Gold DNA Polymerase. PCR was carried out in a total volume of 50 μl. After five minutes of heating at 95° C., the mixture was subjected to 20 cycles of: 95° C. for 30 seconds, 55° C. for 30 seconds, and 72° C. for one minute, and this was incubated at 72° C. for seven minutes, and then rapidly cooled to 4° C. A 3-μl aliquot of the product was assessed by electrophoresis. After subjecting the remaining solution to ethanol precipitation, the amplified DNA fragment was excised.

Identification Method 2: Identification of Cleavage Sites in the HCV Replicon RNA by the C-Tailing Method 5' RACE System (Invitrogen, cat. #18374-058) was partially used in this experiment (the method was performed according to the product manual).

Reverse Transcription of the HCV RNA

1 µl of 2.5 µM Gene Specific Reverse Primer (R6-876-R20; SEQ ID NO: 21; see Table 1) and 1 to 5 µg of the HCV RNA sample were added to a 0.5-ml siliconized tube (Assist, cat. #72.699Z), and then the total volume was adjusted to 15.5 µl with Nuclease-Free Water (Ambion, cat. #9932). This was heated at 70° C. for ten minutes, and then rapidly cooled on ice. 2.5 µl of 10×PCR buffer, 2.5 µl of 25 mM $MgCl_2$, 1 µl of 10 mM dNTP mixture solution (GE Healthcare, cat. #28-4065-51), and 2.5 µl of 0.1 M DTT were added thereto, and this was mixed by pipetting. The mixture was incubated at 42° C. for one minute, and 1 µl of SuperScript II RT was added thereto, and this was mixed. The mixture was incubated at 42° C. for 50 minutes. This was heated at 70° C. for 15 minutes to terminate the reaction, and then allowed to stand at 37° C. 1 µl of RNase mix was added thereto, and this was incubated at 37° C. for 30 minutes.

cDNA Purification Using S.N.A.P. Columns

120 µl of binding solution (6 M sodium iodide) pre-incubated at room temperature was added to the cDNA. The whole mixture was transferred into an S.N.A.P. column, and this was centrifuged at 13,000× g for 20 seconds. The column was washed four times by adding a cold wash buffer and centrifuging in the same way. Then, cold 70% ethanol was added to the column, and this was washed twice in the same way. The last added ethanol was removed, and then the column was centrifuged for one minute. 50 µl of Nuclease-Free Water pre-heated at 65° C. was added to the column, and this was centrifuged at 13,000× g for 20 seconds to elute the cDNA.

dCTP Addition

10 µl of the eluted cDNA was combined with 6.5 µl of Nuclease-Free Water, 5 µl of 5× tailing buffer, and 2.5 µl of 2 mM dCTP (GE Healthcare, cat. #28-4065-51), and this was mixed gently. The mixture was heated at 94° C. for two minutes, and then rapidly cooled on ice. 1 µl of TdT was added thereto, and this was mixed gently, and incubated at 37° C. for ten minutes. After ten minutes, the solution was immediately heated at 65° C. for ten minutes to inactivate TdT. The solution was briefly centrifuged, and placed on ice.

First-Round PCR of C-Tailed cDNAs

TaKaRa Ex Taq (TaKaRa, cat. #RR001A) was used.

5 µl of a template cDNA was combined with 34.5 µl of Nuclease-Free Water, 5 µl of 10× Ex Taq Buffer, 1 µl of 10 mM dNTPs, 2 µl of 10 µM 5' RACE Abridged Anchor Primer (AAP), 2 µl of 10 µM R6 610-R24 reverse primer (SEQ ID NO: 22; see Table 1), and 0.5 µl of TaKaRa Ex Taq Polymerase. PCR was carried out in a total volume of 50 µl. After two minutes of heating at 94° C., the mixture was subjected to 35 cycles of: 94° C. for 30 seconds, 55° C. for 30 seconds, and 72° C. for one minute, and this was heated at 72° C. for five minutes, and then rapidly cooled to 4° C. The first-round PCR product was used as a template for the second-round PCR.

Second-Round PCR of C-Tailed cDNAs

1 µl of the first-round PCR product was combined with 40.5 µl of $ddH_2O$, 5 µl of 10× Ex Taq Buffer, 1 µl of 10 mM dNTPs, 1 µl of 10 µM Abridged Universal Amplification Primer (AUAP), 1 µl of 10 µM R6 536-R20 reverse primer (SEQ ID NO: 23; see Table 1), and 0.5 µl of TaKaRa Ex Taq Polymerase. The second-round PCR was carried out in a total volume of 50 µl. After reaction, a 3-µl aliquot of the product was assessed by electrophoresis. After ethanol precipitation of the remaining solution, the amplified DNA fragment was excised.

Excision and Purification of Amplified Fragments

Fragments of the PCR products amplified in the second-round PCR were excised and purified.

The result of second-round PCR showed the bands of siE-R5 and siDS-50 between 200 bp and 300 bp, and the band of siDS-197 between 150 bp and 400 bp. The bands of these positions were excised from the gel. The DNAs were eluted by electrophoresis at 50 V for one hour using Max Yield NP (ATTO, Model AE-6580). The eluted DNA samples were treated with TE-saturated phenol and then chloroform. After ethanol precipitation, the precipitated DNA samples were used for ligation.

Ligation

The pGEM-T Easy Vector System I (Promega, cat. #A1360) was used. Pellets of the precipitated DNA samples were dissolved in 7 µl of 2 mM Tris (Trizma base; SIGMA, cat. #T1503-1KG)/0.4 mM EDTA (2Na; Dojindo, cat. #345-01865) (T2E0.4), and 1-µl aliquots were electrophoresed in 5% polyacrylamide gel. The DNA concentration was roughly determined based on the co-electrophoresed DNA markers (100 bp DNA Ladder; New England Biolabs, cat. #N3231L). 50 ng of the pGET-T Easy cloning vector was mixed with a sample containing 4.1 ng of DNA, and then T4 DNA ligase was added thereto. This was incubated at 4° C. overnight for ligation reaction.

Cloning

<Chemical Transformation Method> (Carried Out by the Method According to the Product Manual)

One-shot TOP10 competent cells (Invitrogen, cat. # C4040-10) (50 µl/tube) were thawed on ice, and 4 µl of the ligated sample was added thereto. This was mixed gently, and then allowed to stand on ice for 30 minutes. Then, this was incubated at 42° C. for 30 seconds, and rapidly cooled in ice-cold water. 250 µl of Hi-Competence Broth (NIPPON GENE, cat. #319-01343) was added thereto, and this was cultured with shaking at 37° C. for one hour. 150 µl of the culture medium was plated on an LB plate (A) pre-warmed at 37° C. The plate was incubated at 37° C., and colonies were confirmed after ten hours. 250 to 300 colonies were observed. 70 colonies were each inoculated in 10 ml of Rich LB medium (B). The bacteria were cultured with shaking at 37° C. for 13 hours.

LB plate (A): 1% Bacto-tryptone (BD, cat. #211705), 0.5% Bacto-yeast extract (BD, cat. #212750), 1% NaCl (Wako, cat. #191-01665), 0.002N NaOH (Wako, cat. #197-02125), and 1.5% Bacto Agar (BD, cat. #214010)

Rich LB (B): 2.5% Bacto-tryptone (BD, cat. #211705), 0.75% Bacto-yeast extract (BD, cat. #212750), 0.6% NaCl (Wako, cat. #191-01665), and 0.005N NaOH (Wako, cat. #197-02125)

<Electroporation Method>

10 µg of glycogen was added to the sample after ligation, and this was subjected to ethanol precipitation. The sample was incubated at −20° C. overnight, and DNA was precipitated by centrifugation on the next day. The pellet was rinsed with 70% ethanol, and air-dried, and then dissolved in 6 µl of 2 mM Tris/0.4 mM EDTA (T2E0.4). 2 µl of the ligation sample and 50 µl of JM109 were placed in a cuvette, and electroporation was performed under the conditions of 2.5 kV, 200 Ohms, and 25 µFD. The cells were recovered with 450 µl of Hi-Competence Broth, and cultured with shaking for one hour at 37° C. Then, several to 100 microliters of the culture medium were plated on an LB plate pre-warmed at 37° C. The plate was incubated at 37° C. Colonies were observed after ten hours. 70 colonies were each inoculated to 10 ml of Rich LB medium, and cultured with shaking at 37° C. for 13 hours.

<Miniprep (TENS Method)>

1 ml of a bacterial suspension from 10 ml of the Rich LB medium after shaking culture was transferred into a 1.5-ml tube, and this was centrifuged at 15 krpm and 4° C. for one minute. The supernatant was discarded. After vortexing, 300 μl of TENS solution (10 mM Tris-HCl (pH 7.5), 1 mM EDTA, 0.1 N NaOH, 0.5% SDS (sodium dodecyl sulfate; Wako, 191-07145)) was added thereto, and this was mixed gently. Then, 150 μl of 3 M NaOAc (sodium acetate trihydrate; Wako, 198-01055) was added thereto, and this was mixed gently, and centrifuged at 15 krpm and 4° C. for ten minutes. The supernatant after centrifugation was added to 1 ml of 99.5% ethanol. This was mixed well and centrifuged at 15 krpm and 4° C. for ten minutes. The supernatant was discarded, and the precipitated DNA pellet was rinsed twice with 70% ethanol. After air-drying, 15 μl of T2E0.4 containing 0.1 μg/μl RNase A (BOEHRINGER MANNHEIM #1119915) was added thereto, and the pellet was dissolved. 2 μl of the solution was treated with the EcoRI restriction enzyme (TaKaRa, cat. #1040A), and this was electrophoresed to confirm the insert.

Only when the insert was detected, 90 μl of TE was added to the sample. After treatments with TE-saturated phenol/chloroform and chloroform, ethanol precipitation was carried out at −80° C. for 15 minutes. The sample was centrifuged at 15 krmp and 4° C. for ten minutes. The resulting pellet was rinsed with 70% ethanol and air-dried, and dissolved in 20 μl of T2E0.4. Then, 12 μl of 20% PEG/2.5M NaCl (polyethylene glycol #6000; nacalai tesque, cat. #28254-85) was added thereto. This was mixed thoroughly, and allowed to stand on ice for about one hour, and centrifuged at 15 krmp and 4° C., for five minutes. The pellet was rinsed twice with 70% ethanol and air-dried, and dissolved in 60 μl of T2E0.4. The DNA was quantified and then diluted to 100 to 200 ng/μl.

Sequence Analysis

The BigDye Terminator v3.1 Cycle Sequencing Kit (Applied Biosystems, cat.#4337456) and 3130x1 Genetic Analyzer were used.

1 μl of 100 to 200 ng/μl plasmid DNA sample was combined with 1 μl of 1 μM R6 536-R20 reverse primer, 1.5 μl of 5× BigDye Terminator v1.1/v3.1 Sequencing Buffer (Applied Biosystems, cat.#4336697), 1 μl of BigDye Terminator v3.1 Cycle Sequencing RR100 (Applied Biosystems, cat.#4337456), and 5.5 μl of ddH$_2$O. This was mixed and reacted using the PCR System. The reaction conditions were as follows: 95° C. for one minute, and 30 cycles of 95° C. for 30 seconds, 58° C. for 20 seconds, and 60° C. for three minutes, followed by rapid cooling to 4° C.

Sephadex G-50 Superfine (GE Healthcare, cat. #17-0041-01) was placed in wells of MultiScreen-HV (Millipore, cat. #MAHVN4550), and 300 μl of ddH$_2$O was added to each well. This was allowed to stand for about three hours for gel swelling to prepare Sephadex columns. Excess water was removed using a plate centrifuge. The sequencing samples were loaded onto the columns at 10 μl/well, and this was centrifuged at 2,500 rpm and room temperature for five minutes. The samples were collected in a 96-well plate for sequencing. The water was evaporated by incubation at 45° C. for 20 minutes using a plate evaporator. 15 μl of Hi-Di Formamide (Applied Biosystems, cat. #4311320) was added to each well. The plate was heated at 95° C. for five minutes, and then rapidly cooled with ice-cold water.

The plate containing sequencing samples was placed in 3130x1 Genetic Analyzer to analyze the sequences.

Figure 3:
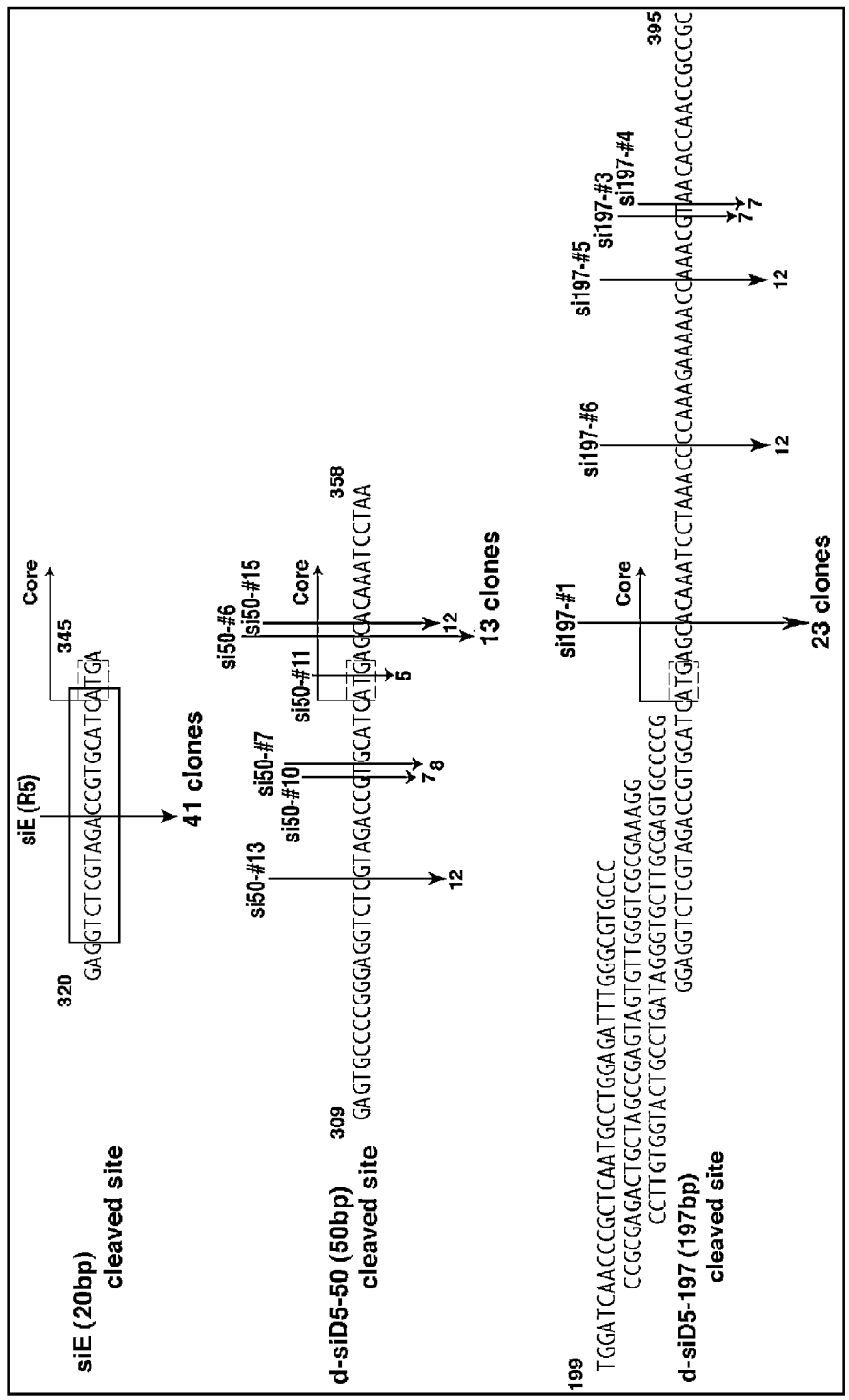
FIG. 3 shows the HCV gene sites cleaved by siRNAs prepared by cleaving the long double-stranded RNAs with the Dicer protein.

In the analyzed sequence information, the junction between an HCV-homologous sequence and the RNA Oligo sequence or consecutive C sequence shows the 5' end of the cleaved HCV sequence. That is, the junction is thought to be a site of HCV RNA cleavage by the diced siRNA (FIG. 3). The number of clones that have the same HCV RNA cleavage site was determined, and siRNAs were designed mainly based on the HCV RNA cleavage sites shared by a larger number of clones. The design method is as follows: an siRNA sense strand is designed to have 9 and 12 nucleotides on the 5' and 3' sides of the HCV RNA cleavage site, respectively, for a total of 21 nucleotides. Meanwhile, an siRNA antisense strand has 11 and 10 nucleotides on the 3' and 5' sides of the HCV RNA cleavage site, respectively, for a total of 21 nucleotides. The designed siRNA sequences are shown in Table 2. The custom siRNA synthesis services by Invitrogen and Dharmacon were used to synthesize the siRNAs.

TABLE 2

| siRNA NAME | siRNA SEQUENCE | SENSE (5' to 3') ANTISENSE (5' to 3') | NUCLEOTIDE POSITION |
|---|---|---|---|
| si50-#6 | 5'- CAUCAUGAGCACAAAUCCUAA-3' | (SEQ ID NO: 1) | 338-356 |
|  | 3'-ACGUAGUACUCGUGUUUAGGA -5' | (SEQ ID NO: 2) |  |
| si50-#7 | 5'- GUAGACCGUGCAUCAUGAGCA-3' | (SEQ ID NO: 3) | 328-346 |
|  | 3'-AGCAUCUGGCACGUAGUACUC -5' | (SEQ ID NO: 4) |  |
| si50-#10 | 5'- CGUAGACCGUGCAUCAUGAGC-3' | (SEQ ID NO: 5) | 327-345 |
|  | 3'-GAGCAUCUGGCACGUAGUACU -5' | (SEQ ID NO: 6) |  |
| si50-#11 | 5'- GUGCAUCAUGAGCACAAAUCC-3' | (SEQ ID NO: 7) | 335-353 |
|  | 3'-GGCACGUAGUACUCGUGUUUA -5' | (SEQ ID NO: 8) |  |
| si50-#13 | 5'- GGAGGUCUCGUAGACCGUGCA-3' | (SEQ ID NO: 9) | 319-337 |
|  | 3'-GCCCUCCAGAGCAUCUGGCAC -5' | (SEQ ID NO: 10) |  |
| si50-#15, | 5'- AUCAUGAGCACAAAUCCUAAA-3' | (SEQ ID NO: 11) | 339-357 |

TABLE 2-continued

| siRNA NAME | siRNA SEQUENCE SENSE (5' to 3') ANTISENSE (5' to 3') | NUCLEOTIDE POSITION |
|---|---|---|
| si197-#1 | 3'-CGUAGUACUCGUGUUUAGGAU -5' (SEQ ID NO: 12) | |
| si197-#3 | 5'- AACCAAACGUAACACCAACCG-3' (SEQ ID NO: 13) | 371-389 |
| | 3'-UUUUGGUUUGCAUUGUGGUUG -5' (SEQ ID NO: 14) | |
| si197-#4 | 5'- ACCAAACGUAACACCAACCGC-3' (SEQ ID NO: 15) | 372-390 |
| | 3'-UUUGGUUUGCAUUGUGGUUGG -5' (SEQ ID NO: 16) | |
| si197-#5 | 5'- AGAAAAACCAAACGUAACACC-3' (SEQ ID NO: 17) | 366-384 |
| | 3'-UUUCUUUUUGGUUUGCAUUGU -5' (SEQ ID NO: 18) | |
| si197-#6 | 5'- UCCUAAACCCCAAAGAAAAAC-3' (SEQ ID NO: 19) | 353-371 |
| | 3'-UUAGGAUUUGGGGUUUCUUUU -5' (SEQ ID NO: 20) | |

Example 2

Assessment of Designed siRNAs for the Replication Inhibitory Activity on HCV Replicons <siRNA Reverse Transfection>

Each siRNA sample was diluted to 0.108 µM with opti-MEM containing 0.23% NaHCO$_3$, and then further diluted to prepare a three-fold dilution series of ten stages. Each sample of the dilution series was added at 10 µl/well in triplicates to a Multiplate 96FII (white) for cell culture (Sumitomo Bakelite Co., cat. #MS-8096W) for luciferase assay and a 96-well plate (BD, cat.#353072) for cytotoxicity assay. The Lipofectamine RNAiMAX Reagent (Invitrogen, cat.#13778-150) was diluted to 1% with OPTI-MEM I containing 0.23% NaHCO$_3$, and added at 10 µl/well to the wells of the 96-well plates into which the siRNAs were aliquoted. This was mixed thoroughly, and incubated at room temperature for 20 minutes to prepare siRNA/Lipofectamine complexes. Lipofectamine RNAiMAX alone was added to control wells. In this Example, HCV replicon cells containing the luciferase gene are R6FLR41-14 cells, FLR3-1 cells, and JFH luc 3-13 cells. These cells were used for siRNA assay. The cell number was determined for each cell line. The cells were suspended in DMEM+GlutaMax-I containing 10% inactivated FCS. In 96-well plates, R6 FLR41-14 and FLR3-1 cells were plated at 5,200 cells/100 µl/well, while JFH luc 3-13 cells were plated at 6,000 cells/100 µl/well. The final siRNA concentrations were 0.5, 1.4, 4.1, 12.3, 37.0, 111.1, 333.3, 1000, 3000, and 9000 µM. The cells were incubated at 37° C. under 5% CO$_2$. After 72 hours, luciferase assay and cytotoxicity assay using WST-8 were performed.

<Luciferase Activity Assay Method>

Luciferase activity was assayed using the Bright-Glo Luciferase Assay System (Promega, cat. #E2620).

In the luciferase assay, the culture medium was discarded from every well of 96-well plates, and replaced with 75 µl of DMEM+GlutaMax-I supplemented with 5% inactivated FCS in each well. 75 µl of the Bright-Glo Luciferase Assay System was added to each well. After one minute of shaking, the luciferase activity was determined using Mithras LB 940 (Berthold).

<Cytotoxicity Assay>

Cytotoxicity was assayed using Cell Counting Kit-8 (Dojindo, cat. #343-07623).

The Cell Counting Kit-8 solution was diluted to 7% with DMEM+GlutaMax-I containing 5% inactivated FCS to prepare solutions for the assay. The culture medium was discarded from every well of 96-well plates for cytotoxicity test. 100 µl of the above assay solution was added to each well. This was incubated at 37° C. under 5% CO$_2$ for one hour. The absorbance at a wavelength of 450 nm (reference wavelength: 655 nm) was measured using a microplate reader (Bio-Rad model 550).

Figure 4:
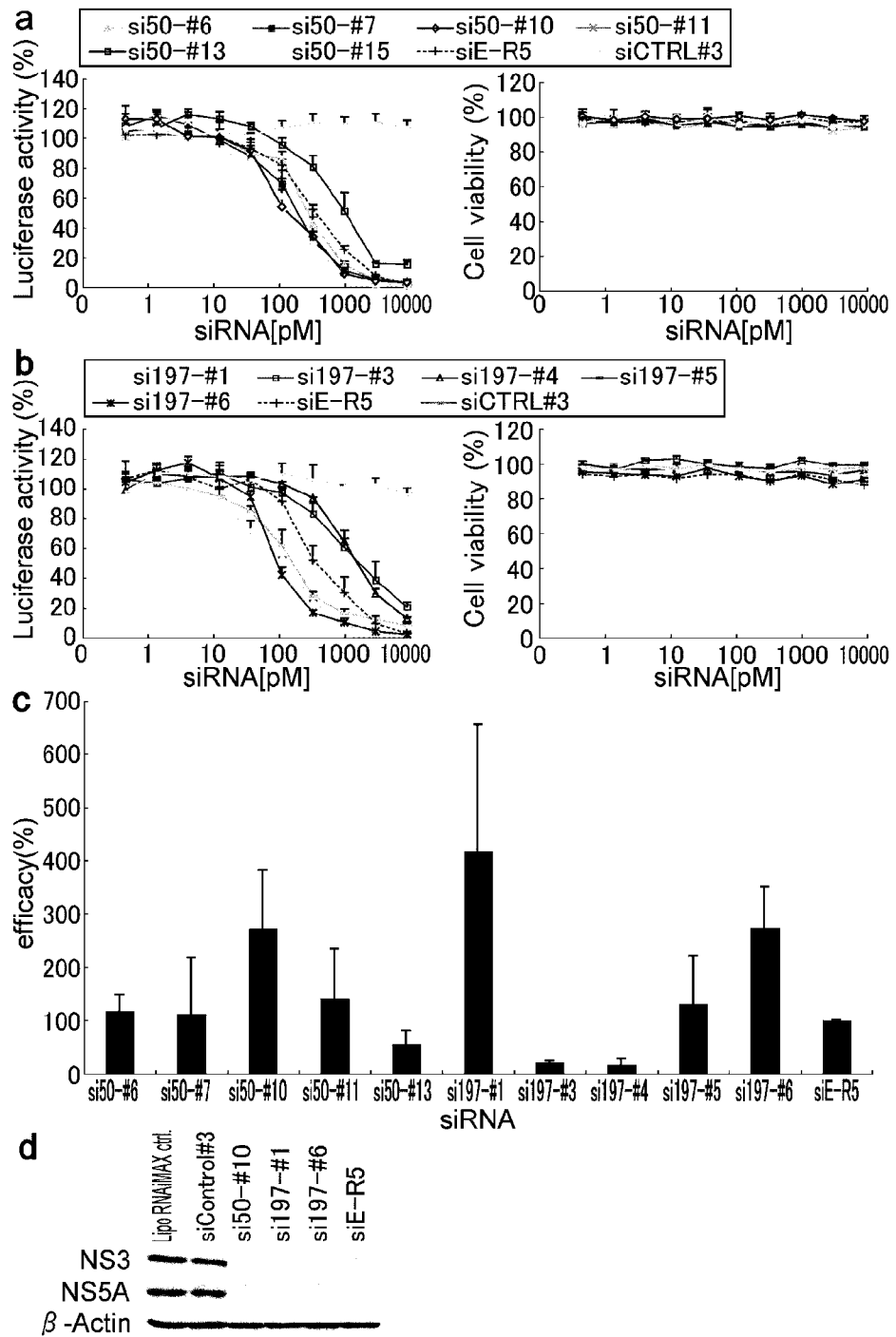
FIG. 4 shows the inhibitory activities of siRNAs produced according to prediction based on the HCV gene sites cleaved by siRNAs prepared by cleaving the long double-stranded RNAs with the Dicer protein.
Figure 5:
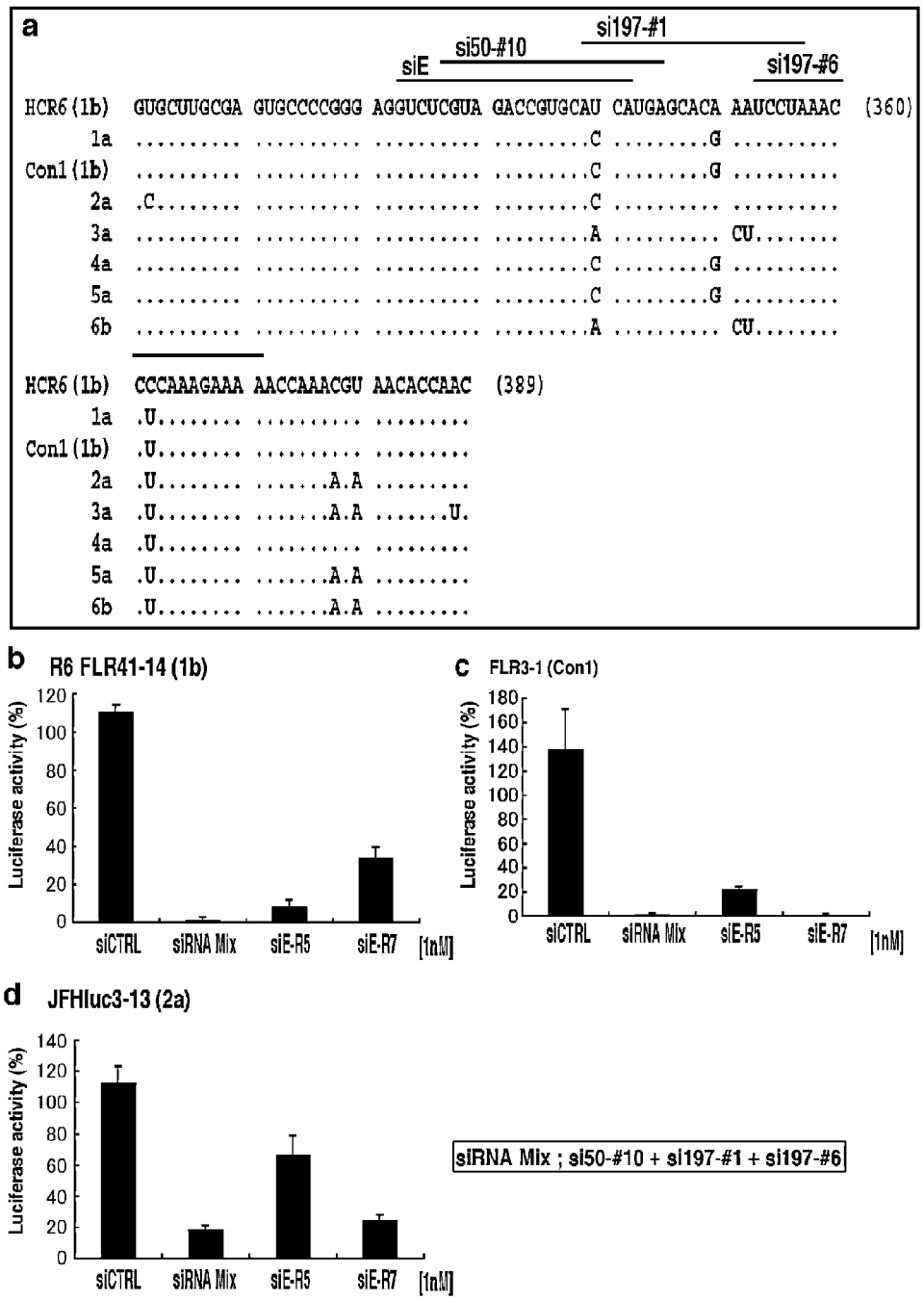
FIG. 5 shows the inhibitory activities of siRNAs on HCV replicons having different nucleotide sequences. The siRNAs were produced according to prediction based on the HCV gene sites cleaved by siRNAs prepared by cleaving the long double-stranded RNAs with the Dicer protein. Even though the nucleotide sequences are different, a strong inhibitory activity was exhibited by mixing three types.
Figure 6:
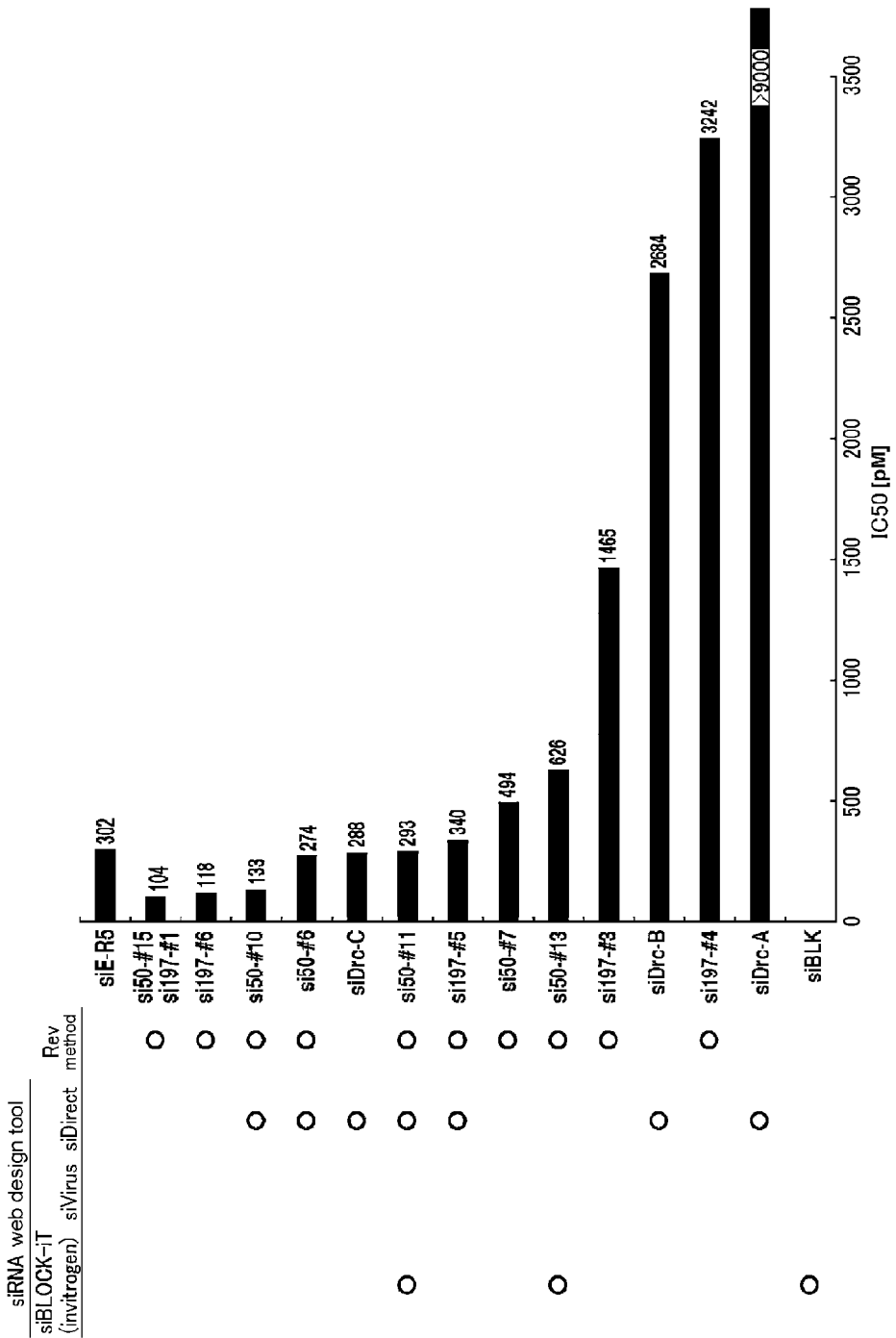
FIG. 6 shows a comparison of the inhibitory activities of siRNAs prepared by the present method (Rev method) and siRNAs prepared using the following computer programs for predicting siRNA sequences: siBLOCK-iT, siVirus, and siDirect. siRNAs prepared by the present method (Rev method) showed the strongest inhibitory activity.

The result showed that si197-#1 and si197-#6 exhibit the strongest replication inhibitory activity on HCV replicons. On the other hand, their cytotoxicity was revealed to be low (FIGS. 4a, b, and c).

Example 3

Assessment of si50 and si197 for the Inhibitory Activity on HCV Protein Synthesis by Western Blotting <siRNA Reverse Transfection>

Each siRNA sample was diluted to 18 nM with opti-MEM containing 0.23% NaHCO$_3$, and this was added to 6-well plates at 500 µl/well. 2.5 µl of Lipofectamine RNAiMAX was added to the siRNAs aliquoted in each well of the 6-well plates. This was mixed thoroughly, and incubated at room temperature for 20 minutes. After counting the number of R6 FLR41-14 cells, they were suspended in DMEM+GlutaMax-I containing 10% inactivated FCS, and plated in 6-well plates at 155,000 cells/2.5 ml/well (the final siRNA concentration was 3 nM). The cells were incubated at 37° C. under 5% CO$_2$. After 72 hours, the culture medium was discarded, and the cells were washed once with PBS(-). Then, PBS(-) was removed by aspiration, and the samples were prepared from the 6-well plates using 60 µl of RIPA (1% SDS, 0.5% Nonidet P-40 (nacalai tesque, cat. #23640-94), 150 mM NaCl, 10 mM Tris-HCl (pH 7.5), 1× Complete (Roche, cat.#11697 498001)) per well.

<Western Blotting>

The above samples were sonicated, and their protein concentrations were determined using the RC DC Protein Assay Reagents (Bio-Rad, cat.#500-0120). 10 µg of the prepared proteins were electrophoresed in a 10% acrylamide gel using a Tris/glycine/SDS buffer. The molecular size markers used were Precision Plus Blue Standard (Bio-Rad, cat. #161-0373) and Broad range Marker (Bio-Rad, cat. #161-0317). The electrophoresed proteins were transferred onto Immobilon-P (Millipore, cat. #IPVH00010) using the Trans-BLOT SD SEMI-DRY TRANSFER CELL (Bio-Rad) at 1 mA/cm$^2$ for 80 minutes. The membrane was blocked with 5% skimmed milk (Snow Brand) for one hour. Then, the membrane was reacted at 4° C. overnight with the NS3 antibody (1 µg/ml, R212 rabbit antibody) or NSSA antibody (rabbit antibody) as a primary antibody. On the next day, the membrane was washed three times with 0.1% Tween/TBS solution for five minutes, and then reacted at room temperature for one hour with the secondary antibody, ECL Anti-Rabbit IgG, HRP-Linked F (ab') 2 Fragment (GE Healthcare, cat.#NA9340) diluted 2000-fold with 5% skimmed milk. Then, the membrane was washed three times with 0.1% Tween/TBS solution for ten minutes. Detection was carried out using the ECL Western Blotting Detection Reagents (GE Healthcare, cat. #RPN2106). β-Actin was detected using a monoclonal anti-β-Actin antibody produced in mouse (SIGMA, cat. #A5441) diluted 5000-fold as a primary antibody, and ECL anti-mouse IgG, HRP-Linked whole Ab (GE Healthcare, cat. #NA931) as a secondary antibody. The result showed that the synthesized si50 and si197 siRNAs inhibit HCV protein synthesis.

Example 4

Assessment of the siRNA for its Inhibitory Effect on HCV Propagation Using an In Vivo System <Preparation of Mice Expressing HCV>

Poly IC (GE, the United States) was administered at 300 µg/head to MxCre/CN2-29 mice expressing a hepatitis C virus every 48 hours for a total of three times (Satoshi Sekiguchi, Yoshimi Tobita, and Michinori Kohara, "C-gata kan-en virus no Jizokukansenkikou to Byogensei (persistent infection mechanism and pathogenesis of hepatitis C virus)", Medical Science Digest. 35 (6): 14-17 2009). Then, the mice were reared for 180 days.

<Therapeutic Experiment Using siRNA>

Liposome-mediated siRNA introduction was achieved using Invivofectamin (Invitrogen). Specifically, 100 µl of Invivofectamin was added to 100 µg of siRNA, and this was mixed gently. The mixture of Invivofectamin and siRNA was shaken at room temperature for 30 minutes using an orbital shaker. Then, 14 volumes of 5% glucose (1,400 µl) were added thereto, and this was mixed. The mixture was centrifuged at 5,000×G and 4° C. or room temperature using Amicon Ultra-15 (Millipore Cat. UFC900308). The concentrated fraction was collected and the volume was adjusted to 2 ml with glucose. 0.2 ml of a liposome administration solution was mixed with the siRNA, and this was intravenously administered to each mouse once on the first day. On day two, the liver was harvested, and then the HCV quantity in the liver was determined using an HCV core quantitation kit (Ortho Clinical Diagnostics).

<Effect Assessment>

Figure 8:
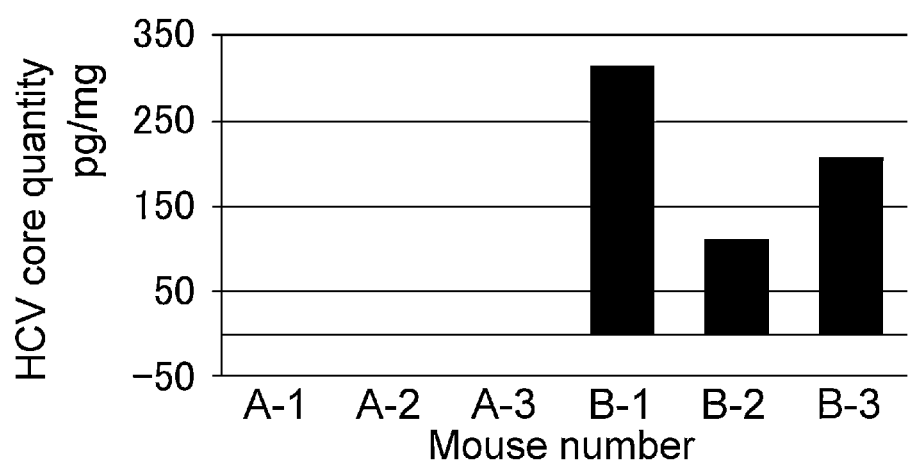
FIG. 8 shows the inhibitory effects of siRNAs on HCV propagation in an in vivo system. B-1 to B-3: the mouse group administered with siSB-Cont#3 at 1 mg/kg 180 days after poly IC induction. A-1 to A-3: the mouse group administered with si197-#1 at 1 mg/kg 180 days after poly IC induction.

The mean HCV core quantity was 211 pg/mg in the control siRNA-administered group (B-1 to B-3; FIG. 8). Meanwhile, the HCV core was not detected in the si197-#1 administration group (A-1 to A-3; FIG. 8). FIG. 8 shows the result of measuring the HCV core quantity in each animal. From the above, it is demonstrated that siSB-197 shows an antiviral effect in HCV-expressing mice in a very short time.

INDUSTRIAL APPLICABILITY

The present invention provides oligoribonucleotides and peptide nucleic acids that inhibit the activity of HCV by binding to HCV RNAs in a sequence-specific manner and more efficiently than those previously identified, and agents for treating hepatitis C which comprise them as an active ingredient. Thus, the present invention provides novel and reliable therapeutic methods against HCVs.

The invention claimed is:

1. A method for designing an siRNA that has efficient RNAi activity against a target gene, which comprises the steps of:
   (i) cleaving the RNA of a target gene or a fragment thereof with Dicer;
   (ii) identifying the cleavage site in the RNA;
   (iii) selecting a sequence that comprises 18 to 23 consecutive nucleotides comprising the cleavage site in the RNA;
   (iv) designing an siRNA comprising the nucleotide sequence selected in step (iii),
   wherein the sense and antisense strands of the designed siRNA have 5 to 12 nucleotides on the 5' or 3' side of the cleavage site; and
   (v) synthesizing the designed siRNA.

2. The design method of claim 1, wherein the target gene is a gene of a host cell.

3. The design method of claim 1, wherein the target gene is a gene of an animal cell.

4. The design method of claim 1, wherein the target gene is a viral gene.

5. The design method of claim 4, wherein the viral gene is an RNA virus gene.

6. The design method of claim 4, wherein the RNA of the target gene or a fragment thereof comprises a sequence that has a higher-order structure and is conserved at a frequency of 80% to 90% or more among strains of the virus.

7. The design method of claim 6, wherein the sequence that has a higher-order structure and is conserved at a frequency of 80% to 90% or more among strains in the RNA of the target gene or a fragment thereof is a sequence comprising an internal ribosome entry site (IRES region).

8. The design method of claim 1, wherein the RNA of (i) has 20 to 400 nucleotides.

9. The design method of claim 4, wherein the virus is HCV, HIV, influenza virus, HBV, dengue virus, measles virus, Norovirus, SARS virus, Rubella virus, poliovirus, RS virus, Marburg virus, Ebola virus, Crimean-Congo hemorrhagic fever virus, yellow fever virus, dengue fever virus, hepatitis G virus, rabies virus, or human T-lymphotropic virus.

10. The design method of claim 5, wherein the RNA of the target gene or a fragment thereof comprises a sequence that has a higher-order structure and is conserved at a frequency of 80% to 90% or more among strains of the virus.

11. The design method of claim 10, wherein the sequence that has a higher-order structure and is conserved at a frequency of 80% to 90% or more among strains in the RNA of the target gene or a fragment thereof is a sequence comprising an internal ribosome entry site (IRES) region.

12. The design method of claim 1, wherein the sense strand of the siRNA is designed to have 9 and 12 nucleotides on the 5' and 3' sides of the cleavage site, respectively, and the antisense strand of the siRNA is designed to have 11 and 10 nucleotides on the 3' and 5' sides of the cleavage site, respectively.

13. The design method of claim 1, further comprising formulating the designed siRNA in a pharmaceutical composition.

14. The method of claim 13, wherein the pharmaceutical composition is formulated for intravenous administration.

15. The method of claim 1, wherein the sense and antisense strands of the designed siRNA have 8 to 12 nucleotides on the 5' or 3' side of the cleavage site.

\* \* \* \* \*